(12) United States Patent
Grobler

(10) Patent No.: US 10,321,681 B2
(45) Date of Patent: Jun. 18, 2019

(54) PLANT SUPPORT FORMULATION, VEHICLE FOR THE DELIVERY AND TRANSLOCATION OF PHYTOLOGICALLY BENEFICIAL SUBSTANCES AND COMPOSITIONS CONTAINING SAME

(71) Applicant: NORTH-WEST UNIVERSITY, Potchefstroom (ZA)

(72) Inventor: Anne Frederica Grobler, Potchefstroom (ZA)

(73) Assignee: NORTH-WEST UNIVERSITY, Potchefstroom (ZA)

( * ) Notice: Subject to any disclaimer, the term of this patent is extended or adjusted under 35 U.S.C. 154(b) by 0 days.

(21) Appl. No.: 14/206,251

(22) Filed: Mar. 12, 2014

(65) Prior Publication Data

US 2014/0194288 A1 Jul. 10, 2014

Related U.S. Application Data

(63) Continuation of application No. 13/441,332, filed on Apr. 6, 2012, now abandoned, which is a continuation of application No. 12/280,880, filed as application No. PCT/IB2007/050580 on Feb. 23, 2007, now abandoned.

(30) Foreign Application Priority Data

Feb. 27, 2006 (ZA) .................................. 2006/01725

(51) Int. Cl.
| | | |
|---|---|---|
| *A01N 37/02* | (2006.01) | |
| *A01N 43/653* | (2006.01) | |
| *A01N 25/04* | (2006.01) | |
| *A01N 37/06* | (2006.01) | |

(52) U.S. Cl.
CPC ........... *A01N 43/653* (2013.01); *A01N 25/04* (2013.01); *A01N 37/02* (2013.01); *A01N 37/06* (2013.01)

(58) Field of Classification Search
CPC ......... A01N 37/02; A01N 37/06; A01N 25/04
USPC ....................................................... 504/313
See application file for complete search history.

(56) References Cited

U.S. PATENT DOCUMENTS

| | | | |
|---|---|---|---|
| 4,567,161 A | 1/1986 | Posanski et al. | |
| 5,362,707 A | 11/1994 | Fiard et al. | |
| 5,504,055 A * | 4/1996 | Hsu ........................ | A01N 59/06 504/121 |
| 5,633,284 A * | 5/1997 | Meyer ...................... | A61K 8/19 514/560 |
| 5,797,976 A * | 8/1998 | Yamashita ................ | A01G 7/06 71/11 |
| 2006/0014645 A1 | 1/2006 | Yavitz et al. | |
| 2006/0105915 A1 | 5/2006 | Naleway et al. | |
| 2007/0078057 A1 | 4/2007 | Rowley et al. | |

FOREIGN PATENT DOCUMENTS

| | | | | |
|---|---|---|---|---|
| DE | 4437945 A1 * | 4/1995 | ............. | A01N 25/32 |
| WO | 99/14293 A | 3/1999 | | |
| WO | 02/05849 A | 1/2002 | | |
| WO | 02/05850 A | 1/2002 | | |
| WO | 03/075656 A | 9/2003 | | |

OTHER PUBLICATIONS

Science Dictionary: Plant Nutrients obtained online on Mar. 6, 2017.*
Notification of a requisition by the examiner in accordance with subsection 30(2) of the Patent Rules dated Sep. 10, 2012, cited in Canadian Patent Application 2,644,354, 5 pages.
Notification of a requisition by the examiner in accordance with subsection 30(2) of the Patent Rules dated Jun. 23, 2014, cited in Canadian Patent Application 2,644,354, 11 pages.
Notification of a requisition by the examiner in accordance with subsection 30(2) of the Patent Rules dated Mar. 27, 2015, cited in Canadian Patent Application 2,644,354, 3 pages.
Notice of Allowance cited in Canadian Patent Application 2,644,354,dated Oct. 9, 2015, 2 pages.
Notification of the First Office Action cited in Chinese Patent Application No. 200780014678.3 dated Oct. 26, 2011, 11 pages.
Notification of the Second Office Action cited in Chinese Patent Application No. 200780014678.3 dated May 12, 2012, 12 pages.
Notification of the Third Office Action cited in Chinese Patent Application No. 200780014678.3 dated Mar. 7, 2013, 7 pages.
Notification of Rejection Decision cited in Chinese Patent Application No. 200780014678.3 dated Jun. 27, 2014, 8 pages.
Notification of Reexamination cited in Chinese Patent Application No. 200780014678.3 dated Jun. 23, 2015, 24 pages.
Notification of Reexamination Decision cited in Chinese Patent Application No. 200780014678.3 dated Dec. 28, 2015, 16 pages.
Communication pursuant to Rules 161 and 162 EPC cited in European Application No. 07713166.2-2103 dated Oct. 16, 2008, 2 pages.

(Continued)

*Primary Examiner* — Mina Haghighatian
*Assistant Examiner* — Mei Ping Chui
(74) *Attorney, Agent, or Firm* — Rothwell, Figg, Ernst & Manbeck, P.C.

(57) ABSTRACT

A plant supporting formulation which is also suitable for use as a delivery vehicle, or a component of a delivery vehicle, for the delivery of one or more phytologically beneficial substances to a plant, and for enhancing the translocation of such delivered substance(s) in or on the plant, the formulation comprising a micro-emulsion constituted by a dispersion of vesicles or microsponges of a fatty acid based component in an aqueous carrier, the fatty acid based component comprising at least one long chain fatty acid based substance selected from the group consisting of free fatty acids and derivatives of free fatty acids. The dispersion is preferably characterized in that at least 50% of the vesicles or microsponges are of a diametrical size of between 50 nm and 5 micrometer. The dispersion is further also characterized in that the micro-emulsion has a zeta potential of between −25 mV and −60 mV.

13 Claims, 9 Drawing Sheets

(56) References Cited

OTHER PUBLICATIONS

Communication pursuant to Article 94(3) EPC cited in European Application No. 07713166.2-1408 dated Mar. 14, 2013, 3 pages.
Noting of loss of rights pursuant to Rule 112(1) EPC cited in European Application No. 07713166.2-1408 dated Oct. 22, 2013, 1 page.
Communication pursuant to Article 94(3) EPC cited in European Application No. 07713166.2-1408 dated Nov. 26, 2015, 5 pages.
First Examination Report cited in New Zealand Application No. 608755 dated May 4, 2013, 2 pages.
Further Examination Report cited in New Zealand Application No. 608755 dated Jul. 7, 2014, 2 pages.
Notice of Acceptance cited in New Zealand Application No. 608755 dated May 11, 2014, 1 page.
Letters Patent for New Zealand Application No. 608755, dated Feb. 23, 2007, 1 page.
First Examination Report cited in New Zealand Application No. 701034 dated May 11, 2014, 2 pages.
Further Examination Report cited in New Zealand Application No. 701034 dated Jul. 20, 2015, 2 pages.
New Zealand Application No. 701034 Notice of Acceptance dated Oct. 14, 2015, 2 pages.
Letters Patent for New Zealand Application No. 701034 dated Feb. 23, 2016, 1 page.
Third Office Action cited in Chinese Application No. 201510629941.6 dated Jun. 13, 2018, 10 pages.
Office Action cited in European Application No. 07 713 166.2 dated Oct. 19, 2017, 4 pages.

* cited by examiner

PLANT SUPPORT FORMULATION, VEHICLE FOR THE DELIVERY AND TRANSLOCATION OF PHYTOLOGICALLY BENEFICIAL SUBSTANCES AND COMPOSITIONS CONTAINING SAME

This application is a continuation of U.S. Ser. No. 13/441,332, filed on Apr. 6, 2012, which is a continuation of U.S. Ser. No. 12/280,880 filed on Oct. 30, 2008, which is a 35 U.S.C. 371 National Phase Entry Application from PCT/IB2007/050580, filed Feb. 23, 2007, which claims the benefit of South African Patent Application No. 2006/01725 filed on Feb. 27, 2006, the disclosure of which is incorporated herein in its entirety by reference.

FIELD OF THE INVENTION

This invention relates to a plant supporting formulation which in itself is phytologically beneficial and which is also suitable for use as a delivery vehicle, or a component of a delivery vehicle, for use in delivering to a plant, and for distributing or translocating in a plant, a variety of phytologically beneficial substances in the form of molecules, compounds, biologicals or chemicals that have a phytologically beneficial effect to plants [herein collectively referred to as "phytologically beneficial substances"]. The expression "plant supporting" is used herein to signify that the formulation has the property, without the addition of other phytologically beneficial substances for which it may serve as a delivery vehicle, to have a growth stimulatory effect on plants in at least one of the growth stages of a plant, to improve the production or yield of crop by the plant, or to improve appearance of the plant or to enhance disease resistance in the plant. It also relates to methods of producing the plant supporting formulation and delivery vehicle, and to the preparation of various formulations incorporating the formulation as a delivery vehicle and any one or more of a variety of phytologically beneficial substances and to methods of administering such phytologically beneficial substances to a plant involving the use of the delivery vehicle of the invention which then also serves to effect the translocation or distribution of the phytologically beneficial substances in or on the plant. It will be appreciated or become apparent that reference to "beneficial effects" as it applies to a plant, is to be understood from a human perspective in that phytotoxic substances, such as substances used as herbicides in the control of undesirable plants, are intended to be included within the group of substances herein referred to as "phytologically beneficial substances".

BACKGROUND TO THE INVENTION

Vast quantities of a great variety of substances are applied to plants for the purpose of enhancing the growth of the plants in order to improve the production (in the case of crop and field plants) or appearance (in the case of ornamentals) of the plants. Such substances include the group defined above as phytologically beneficial substances. It includes fertilizers, both of the macro- and micro-nutrient variety, growth stimulants or regulators, and pesticides, including fungicides, insecticides and herbicides. As used herein the word "plant" is intended to cover land and water plants, including sea plants, and "ornamentals" are intended to cover all plants that are not intended to produce a crop having economic value.

The application of phytologically beneficial substances is generally regarded as an art that is in need of improvement as a large percentage of the applied substances are not absorbed by or retained on the plants to which it is applied. Apart from the consequential wastage of expensive material and hence the unnecessary increase in production cost brought about by such wastage, the unutilized substances also give rise to pollution of the soil and water resources.

There appears to be no reference in the literature to the use of a designed biological delivery system to address the enhanced administration of specific nutrients or growth regulators to plants and/or the systemic translocation of such nutrients or growth regulators throughout the plants. It is known in the agricultural field that nutrients and other phytologically beneficial substances may be formulated with so-called chelating agents or adjuvants. Unlike the present invention the chelating agents are a clearly distinguishable group with no reference to a delivery system and are used as micro-nutrient sources that are formed by combining a chelating agent with a metal through coordinate bonding. Stability of the metal-chelate bond affects the availability to plants of the micronutrient metals—copper, iron, manganese, and zinc. An effective chelate is one in which the rate of substitution of the chelated micronutrient for other cations in the soil is quite low, thus maintaining the applied micronutrient in chelated form. Chelates are generally only applicable to cationic substances. A chelating agent, such as EDTA, is thought to have a negative impact on the environment.

According to prescriptions for chelates in the Preliminary Organic Materials List by the California Departments of Food and Agriculture, natural chelates are allowed but synthetic chelating agents are restricted for use only with micronutrient sprays for a documented deficiency. All other uses of synthetic chelates are prohibited. EDTA, lignin sulfonates and lignosulfonic acids are considered to be synthetic chelating agents. Recently, a shuttle system for the delivery of cations was announced. The shuttle system consists of long chain polysaccharides which can complex with cationic nutrients in clusters (nanoclusters), thus rendering the nutrient-chelate complex neutral. The chelators (shuttle ligand) then envelop the enclustered nutrients and shuttle them to the cell wall where they deliver their nutrients. The delivery are thought to take place through a random process whereby the pores on the plant and the shuttle ligand both contract and expand as a result of a thermal vibration, a natural phenomenon. It is thought that when contraction of the chelator and expansion of the pore synchronize, the nutrient is delivered. Upon unloading the mineral, the shuttle ligand is repulsed from the plant surface, and is attracted back to the nanocluster where it can repeat the process again and again. The shuttle chelating system may extend to other dormant cations in the soil. However, the system is still based on the use of chelates, can complex only to cationic compounds and do not penetrate the plant tissue.

Cloak Spray oil, marketed in South Africa by Nutri-Tech Solutions, is an organic blend of emulsified, cold press canola oil and omega-3 fish oil. Cloak oil is thought to be a high quality spreader, sticker synergist (see below) which is claimed to improve the performance of all foliar fertilizers. However, no claims are made regarding either the translocation of substances within the plant or the delivery of other substances or fertilization by the root system of the plant.

The most established method of introducing material or substances into plant cells is by spraying of the substance in the presence of a wetting agent, spreader or sticker. By this technique material is sprayed onto leaves of plants in the presence of a wetting agent which would cause the material to adhere to the waxy outer layer of leaves, thereby increasing contact time between the material to be absorbed by the plant and the plant leaf itself. While some of the material gets taken up, the wetting agent, which usually contains an adherent, cause the leaves to become sticky and attract dust, which in turn may lead to occlusion of the stomata. Carriers for the agricultural sector have been described but relate to methods of application and not to the enhancement of the action of the active compound due to increased delivery to the target cell or organism. The closest approximation to a delivery system that may be used to overcome barriers to entry in plants are to be found in the use of adjuvants for enhancing the activity of some active compounds in the herbicide and hormone classes.

While these techniques work adequately in the appropriate environment on some compounds that are easily absorbed by leaves, they are not regarded as being generally suitable for the effective delivery of a number of macro- and micro-nutrients, as well as a large number of pesticides and growth regulators. There has thus been a long-felt need for an appropriate process by which compounds may be introduced selectively into plant cells there to enhance growth or to treat plant diseases or deficiencies.

Adjuvants are chemically and biologically active (not chemically inert) compounds and may be classified according to their function (activator or utility), their chemistry (such as organosilicones), or source (vegetable or petroleum oils). They produce pronounced effects. Most adjuvants are incompatible with some materials and conditions and may result in toxic effects in plants and animals, and some adjuvants have the potential to be mobile and pollute surface or groundwater sources. The use of adjuvants may be problematic near water, as adverse effects may occur in some aquatic species.

OBJECT OF THE INVENTION

It is an object of the invention to provide a plant supporting formulation which by itself has beneficial effects in terms of the growth, appearance, production and/or yield of plants to which it is applied in use, and which formulation is also suitable for use as a delivery vehicle, or a component of a delivery vehicle, for the delivery of one or more phytologically beneficial substances to a plant, and distributing or translocating phytologically beneficial substances in plants, to provide for formulations incorporating such vehicles with or without at least one phytologically beneficial substance whereby at least some of the disadvantages of existing formulations may at least be reduced, to provide a method for producing such vehicles and a method of preparing formulations incorporating such vehicles and at least one phytologically beneficial substance, and to provide a method of administering such phytologically beneficial substances to a plant involving the use of the delivery vehicles of the invention which then also serves to effect the translocation or distribution of the phytologically beneficial substances in or on the plant.

GENERAL DESCRIPTION OF THE INVENTION

According to the present invention there is provided a plant supporting formulation which is phytologically beneficial and suitable for use as a delivery vehicle, or a component of a delivery vehicle, for the delivery of one or more phytologically beneficial substances to a plant, and for enhancing the translocation of such delivered substance(s) in or on the plant, the formulation comprising a micro-emulsion constituted by a dispersion of vesicles or microsponges of a fatty acid based component in an aqueous carrier, the fatty acid based component comprising at least one long chain fatty acid based substance selected from the group consisting of free fatty acids and derivatives of free fatty acids.

The dispersion is preferably characterized in that at least 95% of the vesicles or microsponges are of a diametrical size of between 50 nm and 5 micrometer. It will be understood that the vesicles or microsponges in the dispersion are elastic and not necessarily of perfectly spherical shape and accordingly the term "diametrical size" is not to be understood as a term of geometric precision. It is further to be understood that it is not practicable to determine such diametrical size in three dimensions without the use of highly sophisticated instrumentation. It is accordingly to be determined in two dimensions by means of microscopic observation and thus refers to the maximum measurement across observed vesicles or microsponges as seen in two dimensions.

The dispersion is further also characterized in that the micro-emulsion has a zeta potential of between −35 mV and −60 mV.

The fatty acid based component may be selected from the group consisting of oleic acid, linoleic acid, alpha-linolenic acid, gamma-linolenic acid, arachidonic acid, eicosapentaenoic acid [C20:5ω3], decosahexaenoic acid [C22:6ω3], and ricinoleic acid, and derivatives thereof selected from the group consisting of the $C_1$ to $C_6$ alkyl esters thereof, the glycerol-polyethylene glycol esters thereof, and the reaction product of hydrogenated and unhydrogenated natural oils composed largely of ricinoleic acid based oils, such as castor oil, with ethylene oxide.

In one form of the invention the fatty acid component of the micro-emulsion may consist or include a mixture of esterified fatty acids, and in this regard it is preferred to make use of the product known as Vitamin F Ethyl Ester. This product is commercially available under the trade description of Vitamin F Ethyl Ester CLR 110 000 Sh.L. U./g from CLR Chemicals Laboratorium Dr. Kurt Richter GmbH of Berlin, Germany. The typical fatty acid distribution of this product is as follows:

$<C_{16}$: 0
$C_{16.0}$: 8,3%
$C_{18.0}$: 3,5%
$C_{18.1}$: 21,7%
$C_{18.2}$: 34,8%
$C_{18.3}$: 28,0%
$>C_{18}$: 1,6%
unknown: 2,1%

The fatty acid component may alternatively include or consist of the long chain fatty acids known as eicosapentaenoic acid [C20:5ω3] and decosahexaenoic acid [C22:6ω3]. Such a product combination is available from Roche Lipid Technology under the trade name "Ropufa '30' n-3 oil". It has been found useful to incorporate these acids where a hydrophobic substance is desired to be delivered to the plant. An alternative product that may be used for this purpose is one of the group of Incromega products available from BASF.

The fatty acid component may in addition to the aforementioned substances or mixtures of substances also include the reaction product of hydrogenated natural oils composed largely of ricinoleic acid based oils with ethylene oxide. It is preferable for this substance to be produced from castor oil of which the fatty acid content is known to be predominantly composed of ricinoleic acid. This product may be modified as to the extent of hydrogenation, ethylation and the addition of groups such as polyethylene glycol. A range of such products is being marketed by BASF under the trade description of Cremophor of various grades. According to a preferred form of the invention for certain applications there is provided a delivery vehicle in which the Cremophor grade, or other composition of modified ricinoleic acid used, is one in which the ricinoleic acid molecules are modified by the addition thereto of polyethylene glycol groups which comprise between 35 and 45 ethylene oxide units.

The vehicle may incorporate a suitable gas dissolved in the fatty acid mixture, the gas being selected to be suitable to impart the requisite size distribution of vesicles and the requisite zeta potential to the micro-emulsion.

The gas is preferably selected from the group consisting of nitrous oxide, carbon oxysulfide and carbon dioxide.

According to another aspect of the invention there is provided a method for producing a plant supporting formulation or delivery vehicle according to the present invention as defined above, comprising the steps of mixing the fatty acid based component with water to obtain a micro-emulsion, and introducing a suitable gas into the mixture, the gas being selected to be suitable to impart the requisite size distribution of vesicles and the requisite zeta potential to the micro-emulsion.

The mixing of the fatty acid component is preferably effected with heating and stirring, preferably by means of a high speed shearer.

The gas may be introduced into the water either before or after the fatty acid based component of the micro-emulsion is mixed with the water. Thus in one form of the invention the gas may be dissolved in the water to obtain a saturated solution of the gas in water, and the saturated solution of the gas is thereafter mixed with the fatty acid component of the micro-emulsion being prepared. The saturated solution of the gas in water may be prepared by sparging the water with the gas, or by exposing the water to the gas at a pressure in excess of atmospheric pressure for a period of time in excess of the time required for the water to become saturated with the gas. In an alternative form of this aspect of the invention an emulsion of the fatty acid component in water may first be prepared and may thereafter be gassed by exposing the emulsion to the gas. This is preferably done by sparging.

The gas is preferably selected from the group consisting of nitrous oxide, carbon oxy sulfide and carbon dioxide.

The phytologically beneficial substance that may be delivered to a plant by means of the delivery vehicle according to the present invention may be any one or more of the substances known to be useful as a plant nutrient; a plant pesticide including a herbicide, fungicide, bactericide, insecticide, anti-plant virus agent; a plant growth regulator; a plant immune modulator; a biostimulant; or genetic material for the transformation of the plant to allow the incorporation of a new characteristic or property in the plant. Such property may inter alia consist of drought resistance, pest resistance and enhanced fruit production.

A formulation is typically available in forms that can be sprayed on as liquids. It includes the active ingredient(s) of substance(s) as listed in the present invention, any additives that further enhance effectiveness, stability, or ease of application such as surfactants and other adjuvants, and any other ingredients including solvents, carriers, or dyes. The application method and species to be treated determine which formulation is preferable.

The invention accordingly also provides a plant nutrient composition comprising at least one plant nutrient in the delivery vehicle described above. Plant growth in its germination, vegetative or productive phases may be stimulated by enhancing the delivery of nutrients, including nutrients in the gas phase. The plant nutrients may be selected from the group of elements consisting of carbon, hydrogen, oxygen, nitrogen, phosphorus, potassium, calcium, magnesium, sulphur, iron, manganese, zinc, copper, boron, molybdenum and chlorine.

The invention further provides a plant pesticide composition comprising a pesticidally effective concentration of at least one plant pesticide in the delivery vehicle described above. A pesticide is any substance or mixture of substances intended for preventing, destroying, repelling, or mitigating any pest.

Pesticides do not only refer to insecticides, but also to herbicides, fungicides, and various other substances used to control pests. Under United States law, a pesticide is also any substance or mixture of substances intended for use as a plant regulator, defoliant, or desiccant. It is intended to use the term in this broad meaning thereof in this specification.

It is accordingly within the ambit of this application to provide a vehicle for, and to provide formulations that include any one or more phytologically beneficial substances in the form of pesticides selected from the group consisting of the following chemical and biological (organic) pesticides synthetic arsenic, Bt liquid w/xylene, Bt liquid-no xylene, Bt wettable powder, beneficial organisms, biodynamic preparations, bordeaux mixes—copper, hydroxide/fixed copper, boric acid, carbamates, chlorinated hydrocarbons, chromate ions, citric acid, copper hydroxide, copper sulfate, herbal preparations selected from cinnamon, cloves, garlic, mint, peppermint, rosemary, thyme, and white pepper, herbicides—synthetic, hydrated lime, imidacloprid—a neonicotinoid insecticide, indoxacarb (p)—a chiral oxadiazine insecticide, insect extracts, isocyanate, lauryl sulfate, lime sulfur, malathion, malic acid, methyl bromide, methyl sulfoxide, milky spore disease—*B. popillae*, nematocides-synthetic, nematodes, nicotine, oils selected from carrot oil, castor Oil (U.S.P. or equivalent), cedar oil, cinnamon oil, citronella oil, citrus oil, clove oil, corn oil, cottonseed oil, dormant oils, garlic oil, geranium oil, lemon grass oil, linseed oil, mint oil, peppermint oil, rosemary oil, sesame oil, soybean oil, summer oils, thyme oil and weed oils, organophosphates selected from acephate, azinphosmethyl, bensulide, cadusafos, chlorethoxyphos, chlorfenvinphos, chlorpyrifos, chlorpyrifos-methyl, chlorthiophos, coumaphos, ddvp (dichlorvos), dialifor, diazinon, dicrotophos, dimethoate, dioxathion, disulfoton, ethion, ethoprop, ethyl parathion, fenamiphos, fenitrothion, fenthion, fonofos, isazophos, malathion, methamidophos, methidathion, methyl parathion, mevinphos, monocrotophos, naled, oxydemetonmethyl, phorate, phosalone, phosmet, phosphamidon, phostebupirim, pirimiphos-methyl, profenofos, propetamphos, sulfotepp, sulprofos, temephos, terbufos, tetrachlorvinphos, tribufos (def) and trichlorfon, pentachlorophenol, pesticides—synthetic, petroleum distillates, petroleum oil spray adjuvants, 2-phenethyl propionate (2-phenylethyl propionate), pheromones, piperonyl butoxide, plant extracts selected from hellebore, pyrethrum, quassia, sabadilla, citronella, sesame (includes ground sesame plant stalks), eugenol and geraniol, potassium sorbate, putrescent whole egg solids, pyrethroids—synthetic, rock salt—weed control, rotenone, ryania, sea animal wastes, soap based herbicides, sodium chloride, sodium lauryl sulfate, soil fumigants, streptomycin, strychnine, sulfur, virus sprays, and Zinc Metal Strips (consisting solely of zinc metal and impurities).

The invention also provides for a herbicidal composition comprising a herbicidally effective concentration of at least one herbicide in the delivery vehicle described above irrespective of its mode of action and hence includes herbicidal formulations in which the mode of action is any one of the group having the following modes of action, namely:

Auxin mimics (2,4-D, clopyralid, picloram, and triclopyr), which mimic the plant growth hormone auxin causing uncontrolled and disorganized growth in susceptible plant species;

Mitosis inhibitors (fosamine), which prevent re-budding in spring and new growth in summer (also known as dormancy enforcers);

Photosynthesis inhibitors (hexazinone), which block specific reactions in photosynthesis leading to cell breakdown;

Amino acid synthesis inhibitors (glyphosate, imazapyr and imazapic), which prevent the synthesis of amino acids required for construction of proteins;

Lipid biosynthesis inhibitors (fluazifop-p-butyl and sethoxydim), that prevent the synthesis of lipids required for growth and maintenance of cell membranes (Weed Control Methods Handbook, The Nature Conservancy, Tu et al.).

It is accordingly within the ambit of this application to provide a vehicle for, and to provide formulations that include any one or more phytologically beneficial substances in the form of herbicides selected from the group consisting of the following: 2,4-D (2,4-dimethylphenol), Clopyralid, Fluazifop-p-butyl, Flumetsulam—a triazolopyrimidine herbicide, Fosamine Ammonium, Glyphosate, Hexazinone, Imazapic, Imazapyr, Picloram, Sethoxydim, Triclopyr.

It also provides for a fungicide composition comprising a fungicidally effective concentration of at least one fungicide in the delivery vehicle described above. The fungicide may be selected from the group consisting of: 1,3 dichloropropene, 2,5-dichlorobenzoic acid methyl ester, 8 hydroxyquinoline, acibenzolar-S-methyl, *Agrobacterium radiobacter*, ammonium phosphite, ascorbic acid, azoxystrobin, *bacillus subtilis* DB 101, *bacillus subtilis* DB 102, *Bacillus subtilis* isolate B246, Bardac, Benalaxyl, Benomyl, Bifenthin, Bitertanol, Borax, boric acid equivalent, boscalid, bromuconazole, bupirimate, captab, carbendazim, Carboxin, chlorine dioxide, chloropicrin, chlorothalonil, chlorpyrifos, copper ammonium acetate, copper ammonium carbonate, copper hydroxide, copper oxychloride, cupric hydroxide, cymoxanil, cyproconazole, cyprodinil, Dazomet, Deltamethrin, Dichlorophen, Dicloran, didesyl dimethyl ammonium chloride, difenaconazole, dinocap, diphenylamine, disulfoton, dithianon, dodemorph, dodine, epoxiconazole, famoxadone, alkohols, anti-oxidants, Fenamidone, Fenarimol, Fenbuconazole, Fenhexamid, Fludioxonil, Flusilazole, Flutriafol, Folpet, fosetyl-Al, furalaxyl, furfural, guazatine, hexaconazole, hydroxyquinoline sulphate, imazalil, iprodione, iprovalicarb, kresoxim-methyl, lime, lindane, mancozeb, maneb, mefenoxam, Mercaptothion, Metalaxyl, metalaxyl-M (mefenoxam), metam-sodium, methyl bromide, metiram, mineral oil, mono potassium phosphate, myclobutanil, octhilinone, oxycarboxin, paraffinic complex (light mineral oil), penconazole, pencycuron, phosphorous acid, polysulphide sulphur, potassium phosphite, potassium phosphonate, prochlorax zinc complex, prochloraz, prochloraz manganese chloride complex, prochloraz zinc complex, procymidone, profenofos, propaconazole, propamocarb HCl, propiconazole, propineb, pseudomonas resinovorans, pyraclostrobin, pyrimethanil, QAC, Quazatine, Quinoxyfen, Quintozene, salicylic acid, silthiopham, sodium-o-phenol phenate(Na salt), spiroxamine, sulphur, TBTO, Tebuconazole, Thiabendazole, Thiabendazole, thiophanate methyl, thiram, tolclofos-methyl, triadimefon, triadimenol, tributyltin oxide, *Trichoderma harzianum*, Tridemorph, Trifloxystrobin, Triflumuron, Triforine, Triticonazole, Vinclozolin, zinc oxide, Zineb and Zoxamide It also provides for a bactericidal composition comprising a bactericidally effective concentration of at least one bactericide in the delivery vehicle described above. The bactericide may be selected from the bactericides known to be suitable for use on plants to combat bacteria infecting plants.

It also provides for an insecticide composition comprising an insecticidally effective concentration of at least one insecticide in the delivery vehicle described above. The insecticide may be selected from the group consisting of (E)-7-dodecenyl acetate, (E,E)-8,10 dodecadien-1-ol, 1,3 dichloropropene, 3(S) ethyl-6-isopropenyl-9-docadien-1 yl acetate, *Allium sativum, Bacillus thuringiensis* Serotype H-7, *Bacillus thuringiensis* subsp *israelensis, Bacillus thuringiensis* var *aiziwai kurstaki, Bacillus thuringiensis* var *kurstaki, Beauveria bassiana, Bradyrhizobium japonicum, Bradyrhizobium japonicum* WB 74, *Bradyrhizobium* sp Luinus VK, *Bradyrhizobium* sp X S21, *Bradyrhizobium spum*, Chlorpyrifos, Dimilin, E8,E10-dodecadienol, EDB, *Metarhizium anisopliae* var acridium isolate IMI 330 189, *Paecilomyces lilacinus* strain 251, *Rhizobium leguminosarum* biovar phaseoli, *Rhizobium leguminosarum* viciaeTJ 9

*Rhizobium meliloti*, Spinosad, Sulfur, *Trichoderma harzianum*, Z-8-dodecenylacetate, Abamectin, abamectin, acephate, acetamiprid, acrinathrin, aldicarb, alpha-cypermethrin, aluminum phosphide, amitraz, azadirachtin, azinphos-methyl, benfuracarb, beta-cyfluthrin, beta-cypermethrin, bifenthrin, borax, brodifacoum, bromopropylate, buprofenzin, buprofezin, cadusafos, carbaryl, carbofuran, carbosulfan, cartap hyrochloride, chlorphenapyr, chlorpyrifos, citronella oil, clofentezine, codlimone (E,E-8,10-dodecadiene-1-01), copper, coumatetralyl, cryptophlebia leucotreta, cyanophos, cyfluthrin, cyhexatin, Cypermethin, cyromazine, d-allethrin, dazomet, deltamethrin, demeton-S-methyl, diazinon, dichlorvos, dicofol, difenacoum, diflubenzuron, imethoate, disulfoton, emamectin, endosulfan, esfenvalerate, ethoprophos, ethoprophos, ethylene dibromide, etoxazole, fenamiphos, fenamiphos, fenazaquin, fenbutatin, fenbutatin oxide, fenitrothion, fenoxycarb, fenpropathrin, fenpyroximate, fenthion, fenvalerate, ferric sodium EDTA, pronil, fipronil, flufenoxuron, flumethrin, fosthiazate, fumagillin, furfural, gamma-BHC, garlic extract, hydramethylnon, imidacloprid, indoxacarb, lambda-cyhalothrin, lavandulyl, senecioate, lufenuron, magnesium phosphide, mancozeb, maple lactone, mercaptothion, metaldehyde, metham-sodium, methamidophos, methidathion, methiocarb, methomyl, methyl bromide, methyl-parathion, mevinphos, milbemectin, mineral oil, novaluron, omethoate, ortho-phenylphenol, oxamyl, oxydemeton-methyl, parafinic complex (mineral oil), parathion, permethrin, phenothoate, phorate, phosmet, phoxim, pirimicarb, polysulphide sulphur, potassium salts of fatty acids, profenofos, propargite, propoxur, protein hydrolysate, prothiofos, pyrethrins, pyriproxyfen, quinalphos, rape oil, rotenone, silicon based repellent, sodium fluosilicate, spinosad, spirodiclofen, sulfur, tartar emetic, tau-fluvalinate, tebufenozide, temephos, terbufos, tetrachlorvinphos, tetradecenyl acetate, tetradifon, thiacloprid, thiamethoxam, thiodicarb, thiram, trichlorfon, triflumuron, trimedlure, zeta-cypermethrin, zinc phosphide.

It also provides for a viracide composition comprising a viracidally effective concentration of at least one viracide in the delivery vehicle described above.

The viracide may be selected from the viracides known to be suitable for use on plants to combat viruses that infect plants.

The invention further provides a plant growth regulator composition comprising a plant growth regulating effective concentration of at least one plant growth regulator in the delivery vehicle described above. The plant growth regulator may preferably be dl-alpha-tocopherol, or the plant physiologically active isomer thereof, which product is also known as Vitamin E, which presence is particularly useful in regulating the onset of the reproductive phase of plants, i.e. may be used to regulate the onset of the flowering of the plant and hence to advance the fruit bearing phase of the plant. More generally however the delivery vehicle may be used to deliver to a plant any one or more of the products in the group consisting of:

2-(1-2-methylnaphthyl)acetamide; 2-(1-2-methylnaphthyl)acetic acid; 2-(1-naphthyl)acetamide; 2-(1-naphthyl) acetic acid; 2,4-D (sodium salt); 3,5,6 TPA; 4-indol-3-ylbutyric acid; 6-benzyl adenine; alkoxylated fatty alkylamine polymer; alkylamine polymer; aminoethoxyvinylglycine hydrochloride; ammoniated nitrates; auxins; calcium arsenate; carbaryl; chlormequat chloride; chlorpropham; chlorthal-dimethyl; cloprop; cyanamide; daminozide; decan-1-ol; dichlorprop; dichlorprop (2-butoxyethyl ester); dimethipin; dinocap; diquat dibromide; diuron; ethephon; fluazifop-p-butyl; gibberellins; glyphosate-isopropylamine; glyphosate-trimesium; haloxyfop-P-methyl; indolylacetic acid; maleic hydrazide; mepiquat chloride; methylcyclopropene; mineral oil; n-decanol; octan-1-ol; paclobutrazole; paraquat dichloride; pendimethalin; prohexadione-calcium; salicylic acid, sodium chlorate; thidiazuron; trinexapac-ethyl; and uniconazole.

The invention also provides for a method of enhancing the structural and functional integrity of plants or parts of plants.

The invention also provides for a method of administering a phytologically beneficial substance to a plant, comprising the step of formulating the substance in a delivery vehicle according to the invention and as described herein, and applying the formulated product to the plant. The application may be by means of aerial or surface application, either mechanical or by manual spraying, by incorporation in water borne irrigation system, or by trunk injection where appropriate.

The invention also provides for a method of supporting the local defence and acquired resistance of plants according to the mechanism described below by simultaneously supplying precursors for defence signalling molecules, antioxidants, ethylene, oleic acid and hexadecatrienoic acid.

The involvement of salicylic acid (SA) as a signal molecule in local defenses and in systemic acquired resistance (SAR) is well known. SA synthesis is activated by exposure to pathogens or ultraviolet light. Salicylic-acid signaling is mediated by at least two mechanisms, with feedback loops to modulate the effect. These feedback loops may also provide a point for integrating developmental, environmental and other defense-associated signals, and thus fine-tune the defense responses of plants. (Jyoti Shah The salicylic acid loop in plant defense. Current Opinion in Plant Biology 2003, 6:365-371)

Studies had suggested a role for lipid peroxidation in the SA-activated expression of resistance genes. SA activates the expression of α-dioxygenase (α-DOX1). α-DOX1 oxidizes 16-C and 18-C fatty acids, the last of which is a component of the formulation of the invention. In addition, fatty acids 16:3 and 18:3 are precursors for the synthesis of oxylipins, which are potent defense signaling molecules. Various research findings thus indicate that fatty-acid-derived signal(s) are involved in modulating SA-signaling in plant defense (Jyoti Shah The salicylic acid loop in plant defense. Current Opinion in Plant Biology 2003, 6:365-371).

Multiple stimuli can activate SA synthesis/signaling. Chloroplasts/plastids in plants may be the source of signals that affect responses to pathogens. Chloroplast/plastid function/integrity is important for the outcome of plant—pathogen interactions. Chloroplasts/plastids are also important for lipid metabolism and the generation of lipid-derived signals. A lipid signal is required for the activation of at least one of the pathways by salicylic acid. Ethylene, which contributes to fruit ripening and colouring, potentiates signaling through this pathway. Studies show that the presence of oleic acid—a component of the invention—is necessary for the lipid derived signal(s) in both resistance pathways. Furthermore, the genetic suppression of resistance is associated with a lowered content of hexadecatrienoic acid (C16:3). The delivery of the 16:3 by an exogenous source should therefore contribute to plant resistance.

EXAMPLES OF THE INVENTION

The invention will now be illustrated, purely by way of examples with reference to the following non-limiting description of Preparations, Examples and Figures in which FIG. 1 is a graph illustrating the increase in number of nodes on cucumber plants treated by use of the plant support formulation of the invention as described in Example 5;

PREPARATION 1

Figure 1:
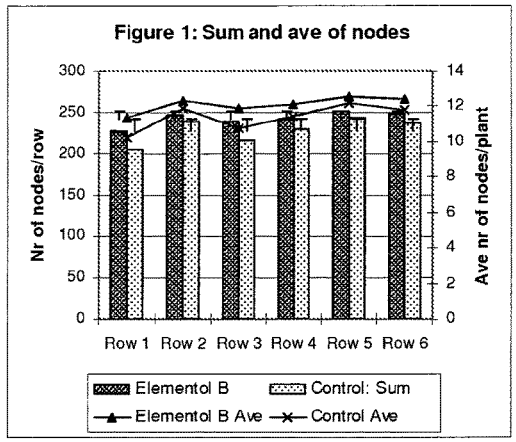

Preparation of Plant Supporting Formulation Suitable for Use as a Delivery Vehicle for Use in Delivering a Phytologically Beneficial Substance to Plants A formulation according to the invention may be made up as follows:

Step 1: A desired volume of water is saturated with the indicated gas (in this example nitrous oxide but the same general procedure with minor modifications is used when employing carbon dioxide) at ambient pressure using a pressure vessel and sparger. The vessel is connected to a supply of nitrous oxide via a flow control valve and pressure regulator. The closed vessel is supplied with nitrous oxide at a pressure of 2 bar for a period of 96 hours, it having been determined that at the aforementioned temperature the water is saturated with nitrous oxide over such period of time under the above-mentioned pressure. In the case of the preparation of the basic or stock formulation (herein referred to as Elementol B) to be used on its own, or when it is to be used as a delivery vehicle for nutrients or the majority of synthetic organic pesticides unchlorinated water is used. Where the stock formulation is intended to be used as a delivery vehicle for peptides or biocatalisators to plants the water is phosphate buffered to a pH of 5.8.

Step 2: The following fatty acid based compositions was made up: First, Vitamin F Ethyl Ester CLR 110 000 Sh·L.U./g obtained from CLR Chemicals Laboratorium Dr. Kurt Richter GmbH of Berlin, Germany which is composed mainly of 21% oleic acid, 34% linolenic acid, and 28% linoleic acid that are modified by esterification with an ethylene group of the carboxy terminal, was heated to 75° C. Secondly, pegylated, hydrogenated fatty acid, ricinoleic acid (also known by the INCI name as PEG-n-Hydrogenated Castor Oil), was heated to 80° C. and mixed with the first group of fatty acid based Vitamin F Ethyl Ester at 70° C. The ratio of the first group of fatty acids to the latter fatty acid was generally 3:1 for foliar application. In the case of the addition of the preparation to large containers supplying plants by drip irrigation in controlled environments on a continuous basis, the ratio was 5:1 to 6:1.

Step 3: dl-α-Tocopherol of varying percentages (final concentration of between 0.1% when used as general anti-oxidant (Elementol B) and 0.25% v/v when used as regulator of plant reproductive phase or for synchronization (Elementol R) was added to the heated fatty acids mixture above, either as anti-oxidant or as growth modulator.

Step 4: The water or buffered water was heated to 73° C. and mixed with the fatty acid mix with the aid of a high speed shearer to a final concentration of between 3.2 and 4%, depending on the specific use of the preparation. This fatty acid mixture constituted the basic preparation that contains vesicles of sizes in the nanometer range as determined by particle size analysis on a Malvern sizer.

Step 5: To the basic preparation may be added additional ethylated fatty acids DHA (decahexonoic acid) and EPA (eicosapentanoic acid). The preferable amount of the two fatty acids for this invention was 0.5%. The addition of these fatty acids results in die formation of microsponges rather than vesicles, with particles between 2-5 µm in size, as determined by particle size analysis on a Malvern sizer.

Step 6: This basic preparation is diluted with water for administration to the plants. The dilutions were generally 1:1 for stem application, 1:10 for ornamentals in open settings, 1:200 for stool beds, 1:600 and 1:800 for orchards, 1:1000 for open field crops and controlled environments, 1:1500 for colouring of fruit, and 1:5000 in hydroponic systems depending on the method of administration, the type of cultivation (e.g. drip irrigation, foliar spraying by hand, tractor or plane).

Stable particles of fairly homogeneous sizes ranging from 50 nm to 50 µm can be manufactured with ease on a large scale. The size and shape of the particles can be reproducibly controlled. The Zeta potential of the Elementol B and Elementol R prepared as described above were determined by means of and found to be −46 mV and −38 mV respectively. Variations in the particle size of the micro emulsions may be effected by varying the composition and variations in the Zeta potential of the emulsion may likewise be effected by varying the composition.

PREPARATION 2

Typical Preparation of a Formulation Containing a Phytologically Beneficial Substance in the Plant Supporting Formulation According to the Invention as a Component of a Delivery Vehicle Step 1: One or more phytologically beneficial substances may be entrapped in the basic Elementol or buffered Elementol preparations described above, by thorough mixing of the desired substance into the Elementol formulation at room or field temperature before dilution for administration as described in step 6 of Preparation 1. Mixing may occur by shaking or stirring. After mixing, preparations are generally allowed to 'cure' for at least 30 minutes, but not more than 3 hours, before dilution with water for administration. In the case of substances with large molecular weights such as peptides, the preparations are left overnight at 4° C.

EXAMPLE 1

Use of Elementol as Delivery Vehicle for Foliar Nutrient Administration on Watermelon Introduction:

Contrary to previous watermelon crops on a selected 160 Ha plot, the watermelon crop of this study had a low yield potential even though there were no changes when compared with previous practices. The following was observed during January 2005:

1.) Premature senescence occurring during January of 2005. It was a scattered phenomenon.
2.) The latter was mainly ascribed to nematodes resulting in the reduction of root efficiency. This resulted in many fruits becoming deformed and suffering "blossom end rot".
3.) Foliar fungal infections were common, irrespective of the pro-active application of fungicides on a 10 day basis. The fungicides were alternated to reduce the risk of resistance by the fungi.

Trial:

The decision was made to maintain the fungicide program, but to introduce a nutrient application as a foliar spray.

The experimental spray, per hectare, contained the following:

5 kg $CaCl_2$ dissolved in 26.0 liters of water.
1.0 liters of "amino acid complexed Calcium" (100 g/liter Ca)
0.5 liters of "amino acid complexed Copper" (75 g/liter Cu)
6 ml Elementol B The concept had the following as objectives:

1.) To boost the plants' internal resistance to the fungal infection with the copper and Elementol B and
2.) To have calcium available at the "meristem", to improve "cell wall integrity" during any future foliar and root development, resulting potentially, in additional fungal resistance and improved foliar and root efficiency.

The Elementol B was added to the amino acids and the blend was allowed to "cure" for 15 minutes before dilution. The dilution was done by adding 28.5 liters of the $CaCl_2$ water. The $CaCl_2$ water was prepared 48 hours in advance.

The purpose for the advance dissolution of the $CaCl_2$ was to subject the chlorine to "UV" hoping to have a reduced effect of this element during the trial. The 1.56 liter "amino acid/Elementol blend", along with the 28.5 liters "Ca-enriched" water resulted in a total of some 30 liters of the preparation being applied per hectare. Application was by aerial foliar spray.

The same application was repeated 10 days later, having increased the Elementol B in the preparation to 12 ml/ha.

Control:

The control strips were treated identically to the trial strips, but excluded the Elementol B.

Repetition:

Since both the trial and the control received two aerial applications, repetition integrity was obtained by using a SATLOC differential global positioning system (DGPS). This instrument was mounted on the aircraft as standard equipment. Each "spray run" during the first application was saved. This allowed for the second application to be applied with less than 0.5 meter deviation from the first application.

Observations:

Within 48 hours of the first application, there was a visual difference between the treated strips and those of the control. The trial strips showed signs of "rejuvenation". The treated plants showed up a much darker shade of green compared to the control. At the same time these plants were showing an observable increase in flowering compared to the control. This phenomenon prompted the grower to request a second application with an increased Elementol B component (12 ml/ha).

Both applications were done during January 2005.

The Elementol B treated watermelons, irrespective of the very low applied volumes (6 ml & 12 ml respectively), senesced well after the control. This delay in senescence varied between 2 to 5 weeks. Although deforming amongst fruit was not reduced by this treatment, it did significantly reduce the blossom end rot.

Due to the scattered occurrence, across the field, of the initial problem, only observations were made.

EXAMPLE 2

Use of Elementol B as Delivery Vehicle for Foliar Administration of Fungicide on Sugar Beans Introduction:
Planting of Sugar beans on a 120 Ha plot was done on seedbeds measuring 910 mm apart (old 3 feet spacing).
Trial:
This trial had the following as objective:
Spraying Elementol B as a foliar application together with a fungicide, by tractor, to observe any reaction by the plants with regards to flowering/yield.
For the trial, an area of 10 hectares was demarcated, using GPS technology and ground markers.
The experimental spray, per hectare, comprised of the following:
200 liters of water
40 ml of Elementol Basic
250 ml Punch® C
Control:
The control area comprised of 10 hectares on the same block. A buffer area of 30 meters separated trial and control. The spray applied here contained no Elementol.
Repetition:
Provision was made for repetition by demarcating both trial and control blocks using GPS technology and ground markers. Two sprays were administered.
Observations:
Sampling the pods was done by hand. The sampling method used was 10×10 meter random rows. This method was also used to sample the control.
Conclusion:
The sampling result was as follows:
Punch® C with Elementol B: 2.390 kg/ha
Punch®, no Elementol: 2.180 kg/ha
Subsequent studies showed that Elementol B contributed to the antifungal effect, as well as to the yield improvement.

EXAMPLE 3

Determination of Phytotoxicity and Beneficial Effects of Elementol R by Foliar Administration on Strawberries Introduction:
The planting of the strawberries on the 12 ha trial plot commenced during early April 2005. The plant material is all first generation. The planted blocks slope down in a westerly direction and the elevation is roughly 100 meters above mean sea level. The soil has a clay content of less than 5% and an organic carbon content of 0.5%.
Trial:
This trial had the following as objective:
Spraying Elementol R as a foliar application, by tractor, to observe any reaction of the plants with regards to flowering.
The experimental spray, per hectare, comprised of the following:
200 liters of water
250 ml of Elementol R
The spraying was done under the following conditions:
Temperature: 23° Celsius (The Δ between wet and dry bulb: <5° C.)
Humidity: 28%
Droplet distribution: averaging 15/cm$^2$
Treated blocks: Blocks 6 & 7
Control block: Block 5
Physiology: Spraying commenced only once 20% of the plants initiated flowering.
Control:
Closing the control tunnel #5 during the application of the Elementol R to blocks 6 & 7 prevented contamination by drift.
Observations:
The two treated blocks, by random sampling, yielded in access of 100% more flowers than the control block. This observation was made 21 days after application. No signs of phytotoxicity were observed.

EXAMPLE 4

Use of Elementol B as Delivery Vehicle for Foliar Boric Acid Administration on Citrus (Navel Var. Lina)

Introduction:
The trial orchard was a 15 Ha orchard on which the trees are about 12 years old, meaning that the trees are mature. The plant population per hectare is 617 trees/ha. Lina navels is an early variety. Getting these to the market first has great financial advantages to the grower.
High levels of gibberellic acid, within fruit bearing plants, results in delayed colouring of fruit. Field experience indicated that the vegetative growth rate of most plants may be reduced by applying, as a foliar spray, a calculated volume of Boron. The Boron source generally used was boric acid ($H_3BO_3$).
At the same grower, during the trial season, Boric acid was applied, in a calculated fashion, to lemons that have been over-nitrified. Over-nitrification of lemons leads to vigorous growth with a reduction in fruit formation. Harnessing this growth phenomenon was achieved using boric acid.
Trial:
Having achieved the inhibition of vigorous growth with boric acid on the lemons, it was assumed that such an application in combination with Elementol B may result in early colouring of Navels on the trees thus saving on de-greening with ethylene in a controlled atmosphere chamber.
This trial was set out on Navels, variety Lina. The surface area was 15 hectares. The objective was early colouring on the trees. No controls were demarcated within the trial area. Orchards of growers adjacent to the trial were monitored as a possible control.
The experimental spray, per hectare, comprised of the following:
2000 liters of water
130 ml of Elementol B
1 kg Boric acid
The boron was dissolved/suspended in water prior to adding the Elementol. A curing time of 30 minutes was allowed before the water was added for final dilution.
Observations:
The treated Linas changed colour on the trees approximately 2 weeks earlier than the adjacent controls. These navels were picked a week earlier than any other in the vicinity

EXAMPLE 5

Controlled Environment Investigations into the Impact of Elementol R on Cucumber Plant Yield Materials and Methods:
Materials
Dicla plastic-covered tunnels (2 um thick plastic with inherent UV-protection for plants) with 2×50001 tanks and pumps, saw dust growth medium, 15 liter plastic bags, seedlings (cucumber) from Dicla, South Africa, Green pepper seedlings from King Athur, Stihl mistblower, calcium nitrate from Ocean or Omnia (South Africa), NutriVeg (Omnia) or HydroGro (Ocean), nitric acid (Ocean), potassium sulphate (Ocean).

Methods:

General set-up: One tunnel and tank each were allocated to the test product, and one tunnel and tank each was used as control. The tunnels were cooled by air cooling with opening and closing of flaps. Flaps and doors were usually closed at between 18:00 and 19:00 for the night, and opened at between 06:00 and 08:00 every morning, depending on temperature. The orientation of the tunnels was north to south, catering for the prevailing wind direction to assist with cooling. No artificial heating or cooling system was used in the tunnels.

Plants:

Cucumbers: 720 Cucumber seedlings of 3 weeks old were transplanted from seedling trays to plastic bags containing saw dust in each of the tunnels at the start of summer. Planting were done in 6 rows of 120 plants per row. The strongest plants were selected for the control tunnel.

Green peppers: 500 King Arthur seedlings were planted in 10 liter plastic bags filled with saw dust in the test tunnel, while 504 similar seedlings were planted in 15 liter plastic bags filled with saw dust. The plants were grown outside the tunnels for the first 2 months without any addition of Elementol R, and then moved to the tunnels, for their pepper-bearing season. Addition of Elementol R to test plants was started two weeks after the transfer of the plants from the outside to the tunnels. A significant difference in yield of green peppers was observed in the test. The possibility was investigated that plants may just be happier inside the test tunnel for reasons other than the treatment with Elementol R. To control for this possibility, Elementol R treatment was interrupted for a 10 day period (day 120-130), after which it was resumed.

Irrigation:

Cucumbers: Small plants received 15 minutes of drip-irrigation 3 times a day through 4 liter/hour drippers, thus a total of 3 liters/day. The irrigation was increased to 30-40 minutes/day (>4 liters/day) after 6 weeks, when plants started bearing fruit that could be harvested and to accommodate the high summer temperatures of up to 45° C. inside the tunnels.

Peppers: Treatment of small plants were similar to that of the cucumbers, but the volume of irrigation was increased after 8 weeks to >5 liters/day/plant.

Test Product:

The test product is a plant beneficial delivery system, called Elementol R. It was hypothesized that this system may increase
a) the solubility and
b) the absorption of nutrients, and more specifically calcium.

The test product was administered by root irrigation. Elementol R was mixed with the nutrient of the tank that supplied irrigation to the test tunnel.

The nutrient mixture for irrigation was as follows:

To each tank filled with 5000 l of borehole water, 500 ml nitric acid was added to lower the pH to 6.0, after which 2 kg of nutrient mix and 2 kg Calcium nitrate were pre-mixed with water and added to the tank in that order. For the test tank and tunnel, pre-mixing was with 1 l of Elementol and water. In the case of the green peppers, 500 g of the calcium nitrate was replaced with 500 g of potassium sulphate when the plants started bearing fruit. Every two weeks, 100 ml of a disinfectant such as Prasine, were added to the full tank to prevent growth of algae. Every $4^{th}$ day, the plants were flushed with borehole water only, after which nutrient feeding continued.

Analysis:

Cucumbers:

The following parameters were investigated during the various phases of plant growth:
i) Plant length
ii) Leaf length
iii) Nr. of nodes
iv) Cucumber yield Plant Length: During the initial growth period it is possible to measure plant length. Twenty randomly selected plants of each row (120 plants for each tunnel) were measured for length from the level of the saw dust to the highest branching from stem. The plastic bags of the plants measured were marked with lime, to prevent repeated measurement of the same plants. The average length of the plants in each row was calculated and used for comparison.

Leaf Length of the bottom two leaves of a plant were determined, using a similar number of plants and selection and calculation procedure as described for plant length.

Number of Internodes: The number of branches formed was counted, using a similar number of plants and selection and calculation procedure as described for plant length.

Cucumber Yield: The cucumbers were harvested. Only those cucumbers fit for sale in an upmarket chain store were counted and weighed. Cucumbers that were bent, yellow or of which the general appearance were not according to sales requirements, were not taken into account.

Green Peppers:

The green pepper experiment was stopped due to the approach of winter. An electrical heating system installed in the tunnels proved to be insufficient and plants were exposed to temperatures below 2° C. Only the saleable yield was determined for the green peppers.

Results and Discussion:

Cucumbers:

Plant length was determined for 120 randomly selected seedlings at ages of 4, 5, and 6 weeks after transplantation. The average length, representing average growth for each tunnel was calculated. Table 1 illustrates the average weekly growth of the seedlings. Whereas the average control plants were initially taller (week 4) than the plants of the test tunnel, the plants that were irrigated with the added Elementol R, grew faster than that of the control tunnel as determined two weeks after the start of the Elementol R treatment.

TABLE 1

| | Average growth in length (cm) | |
|---|---|---|
| Weeks | Elementol | Control |
| 4 | 4.08 | 4.5 |
| 5 | 6.33 | 6.45 |
| 6 | 13.04 | 12.9 |

FIG. 1 illustrates the increase in number of nodes by the addition of Elementol R to the nutrient mix 3 weeks after transplantation of the seedlings and initiation of treatment. The nodes were determined for 20 randomly selected plants in each of the 6 rows, taking care that different plants were used than for the length determination. In each row, the plants treated with Elementol R contained more nodes after 3 weeks of treatment, although the increase was less than 1 (0.73) node per plant when averaged. The standard error is smaller for the plants that were irrigated by the Elementol-nutrient mixture, indicating a synchronizing effect on plant growth.

When an increase of 0.73 nodes per 3 weeks of treatment are projected to a total growth period of 18 weeks, the average difference in number of nodes/plant as a result of Elementol R administration is 4.4 nodes/plant, which is statistically significant. The importance of increased nodes is that it indicates the number of both leaves and fruit-bearing buds that the plant will develop.

Figure 2:
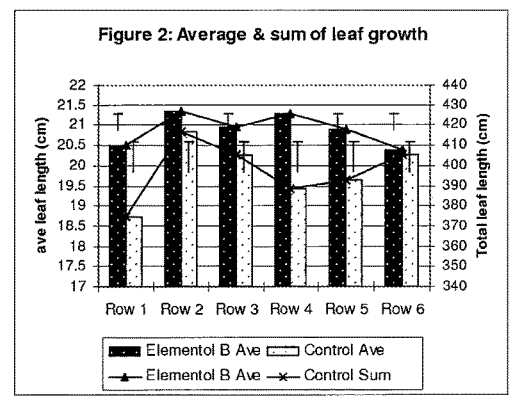
FIG. 2 is a graph illustrating the increase in leaf size of cucumber plants treated by use of the plant support formulation of the invention as described in Example 5.

FIG. 2 illustrates the increase in leaf size by Elementol R root administration. Leaf length was determined for 120 plants in each tunnel; 20 plants per row three weeks after the start of Elementol R administration. As is the case with plant length, the sizes of the leaves of the plants in the test tunnel were slightly smaller than that of the control plants before Elementol administration was started. The difference in leaf size caused by Elementol treatment is significant and is important in the development of the plant, since the leaves are responsible for the photosynthesis. Once again, the standard error was smaller for the plants that received Elementol R.

Figure 3:
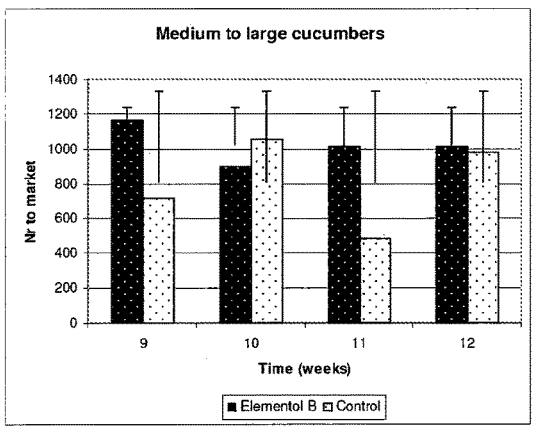
FIG. 3 is a graph showing the numbers of medium to large cucumbers harvested at different times from plants treated with a plant support formulation according to the invention compared to untreated control plants as described in Example 5.
Figure 4:
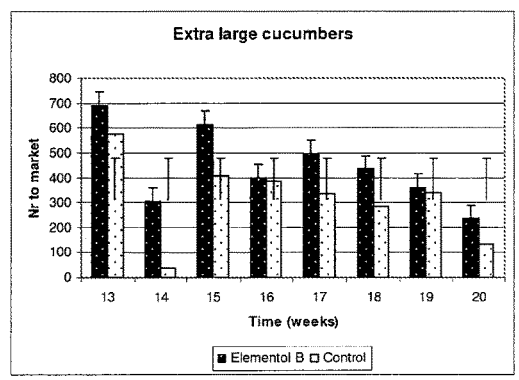
FIG. 4 is a graph showing the numbers of extra large cucumbers harvested at different times from plants treated with a plant support formulation according to the invention compared to untreated control plants as described in Example 5.
Figure 5:
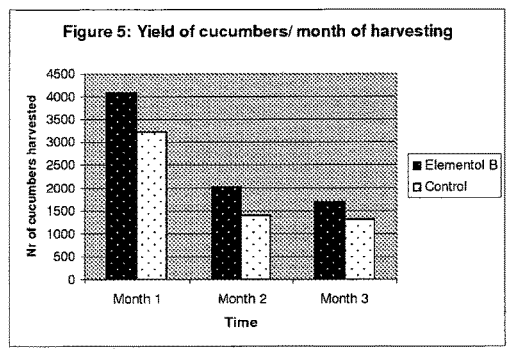
FIG. 5 is a graph showing the total numbers of cucumbers harvested at different times from plants treated with a plant support formulation according to the invention compared to untreated control plants as described in Example 5.

It is generally accepted that the period of yield for cucumbers is 12 weeks, although some producers harvest fruit for a period of 16 weeks. In FIGS. 3 and 4 the yield of the plants over a 12 week period is illustrated, thus plant age as illustrated below is the summation of:

3 weeks from seeding to seedling growth (untreated)+3 weeks of a pre-harvesting Elementol R treated growth+12 weeks of harvesting with Elementol R treatment. Although plants were still producing flowers at week 20, the investigation was stopped at that point, due to a heavy white fly infestation in the absence of a formal pesticide program.

At the start of harvesting, cucumbers were classified as medium to large (up to 37 cm). However, by the end of the $4^{th}$ week and up to the $20^{th}$ week of harvesting, the cucumbers harvested were between 41 to 47 cm in length, resulting in a lower number of cucumbers, but a better harvest in terms of weight. For that reason, the results on yield are separated for the two time periods.

It is necessary to remark that harvesting of the two tunnels occurred simultaneously, and therefore the yield is linked to specific days of the week. This may be slightly artificial, as harvesting of the control tunnel 3 days later than the test tunnel, may have given a more equal distribution of cucumber yield for weeks 9 to 13. During week 14, a breakdown of the electrical supply to the irrigation and pumps over a 48 h period caused a significant decrease in yield in both control and Elementol-treated plants. The stress caused by non-irrigation seemed to be better tolerated by the Elementol-treated plants, as can be seen from FIG. 4.

Table 2 shows the total difference as well as % difference between the yields in cucumbers from the two tunnels.

TABLE 2

| | Difference in yield | |
|---|---|---|
| | Experimental | Control |
| Sum | 7797 | 5941 |
| % of total | 56.75498617 | 43.24501 |
| Ratio | 0.761959728 | |
| % diff | | 31.24053 |
| Nr/month | 3898.5 | 2970.5 |

TABLE 2-continued

| | Difference in yield | |
|---|---|---|
| | Experimental | Control |
| Nr/plant/mnth | 5.414583333 | 4.125694 |
| Fruit/plant | 16.24375 | 12.37708 |

Figure 6:
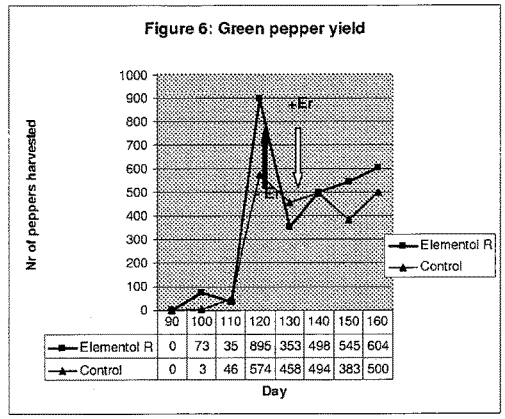
FIG. 6 is a graph showing the numbers of green peppers harvested at different times from plants treated with a plant support formulation according to the invention compared to untreated control plants as described in Example 5.
Figure 7:
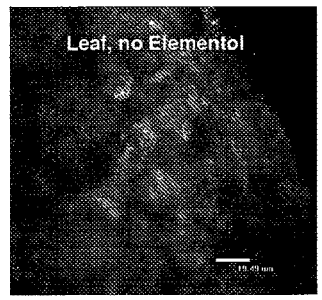
FIGS. 7, 8, 9 and 10 are micrographs of sections of baby marrow plants treated with plant support formulations according to the invention as described in Study 1 of Example 6.
Figure 8:
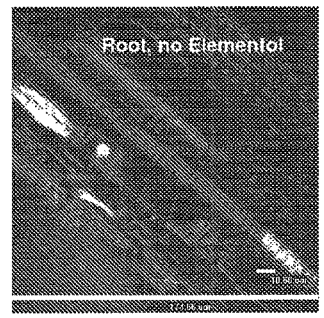
Figure 9:
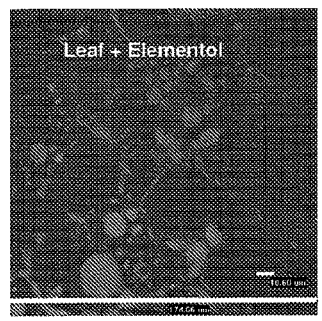
Figure 10:
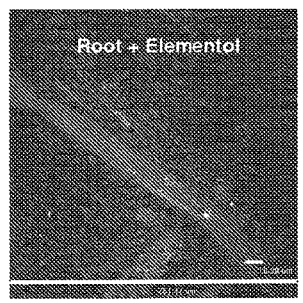
Figure 11:
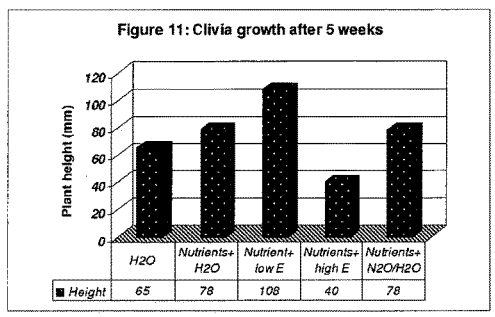
FIGS. 11 and 12 are graphs illustrating the growth of Olivia plants treated with different plant support formulations according to the invention as described in Study 2 of Example 6.
Figure 12:
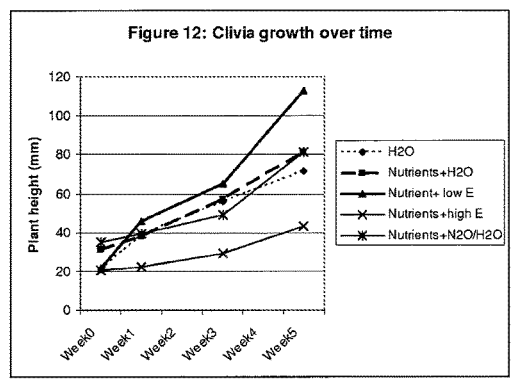

Green Peppers:

FIG. 6 illustrates the yield of the green peppers over a 70 day period. Harvesting was started 3 months (90 days) after planting, whilst treatment with Elementol R started two weeks pre-harvesting. After day 160, plants were exposed to such low temperatures that the experiment was stopped, although the plants were still producing harvestable fruit.

The impact of Elementol R on the yield of green peppers is illustrated in FIG. 6. The first arrow indicates the start of the 10 day interruption of treatment with Elementol, whereas the second arrow indicates when Elementol R treatment was resumed. Each point indicates the combined harvest for that tunnel over a ten day period. A decrease in yield is immediately observable after interruption of Elementol R treatment in the test tunnel. The yield decreased and stabilized at a level similar to that of the control tunnel, indicating that the increased yield can be specifically ascribed to the presence of the Elementol R.

Table 3 shows the total yield and % difference in yield per tunnel.

TABLE 3

| | Difference in yield | |
|---|---|---|
| | Experimental | Control |
| Total | 3003 | 2458 |
| % of total | 54.98993 | 45.01007142 |
| % difference over total period | 22.1725% | |
| % difference before treatment interruption | 42.35294% | |

The determination of the % difference between the two groups can in reality only be made for the time period before the interruption of treatment, since it is difficult to estimate the long-term effect of such an interruption.

Conclusion

The impact of Elementol R on the yield of fruit of two different plant species was investigated—that of cucumbers and green peppers. The addition of Elementol R to the plant nutrients mixture resulted in statistically significant increases of yield of harvestable fruit in both plant species.

EXAMPLE 6

Penetration and Distribution in Dicothyl Plants—Investigation into the Potential of Elementol B Technology for Agricultural Applications The background to the projects is as follows:
Background to the Study Elementol B consists mainly of a function-specific number and combination of unsaturated fatty acids and nitrous oxide.

Preliminary studies were undertaken to determine 1) the permeation/penetration of Elementol B into plants and the translocation of Elementol B in the plants over time and 2) the possible contribution of Elementol B to the delivery of plant nutrients to plants.

Methods and Materials:

Elementol Preparation:

45 g Basic Elementol medium was diluted with 225 g nitrous oxide saturated purified water ($N_2O$—$H_2O$) at room temperature. The mixture was shaken vigorously and 1250 µl of the fluorescent marker Nile Red (1.6 µg/µl; Molecular Probes, Holland) was added.

Study 1

Test Subjects:

Hydroponically cultivated (n=3) baby marrow plants (dicothyl) in bloom stage planted in bags containing wood chips (support medium) were obtained from a nursery for this pilot study. Plants were allocated as follows:

Plant 1: Control—Nothing administered.

Plant 2: Addition of 100 ml prepared Elementol mixture to the support medium bag with wood chip to investigate root application.

Plant 3: The whole plant was sprayed with the Elementol mixture except for one leaf which was covered with plastic before spraying.

After the administration of the Elementol mixture as described above, the plants received no further nutrients but were watered daily. After 3 weeks, harvested baby marrows were compared in terms of size and weight.

Permeation/penetration and Translocation Visualization:

Leaves were dissected to obtain plant tissue from locations devoid of prominent veins as well as crosscuts from prominent veins. Root dissections were performed along the length of the superior root. The absorption and translocation of the fluorescently labelled Elementol were visualized by Confocal Laser Scanning Microscopy on a Nikon PCM2000 with an inverted Nikon Eclipse 300 microscope, equipped with Spectra Physics Krypton/Argon and Helium/Neon lasers. The following objectives were used—Plan Apo 100×/1.4 Oil DIC H; Plan Apo 60×/1.4 Oil DIC H; and a Plan Fluor/0.75 DIC M. Confocal images (micrographs) were digitally captured via fluorescence detectors and photomultupliers. Real time micro-imaging was done with a Nikon DMX video camera system. Depth studies were obtained using a 3D scanning head in combination with a depth z-step drive.

Results:

The results are illustrated in the micrographs obtained by confocal laser scanning microscopy.

Plant 1: In this micrograph, no Elementol was administered to the plant. Material is visualized because of autofluorescence.

Plant 2: Elementol R (pre-labeled with the red fluorescent marker Nile Red) were absorbed by the plant through the leaves and is visible in cross sections of prominent veins of both the covered as well as the treated parts and in dissections of the leaves. In this micrograph, nearly all vesicles of the Elementol have permeated the cells of leaf itself, with few of the Elementol vesicles remaining in prominent veins of the plant. Leaf penetration and translocation throughout the leaves occurred in less than 60 minutes (average time approximately 20 minutes).

Plant 3: Vesicles of Elementol B penetrated the plant through the roots and are visualised in the root segments as well as the cross sections of prominent veins. Root permeation and translocation were observed in less than 60 minutes.

The weights found for the first baby marrows harvested are given below:

Plant 1: Although several flowers were observed on this plant, no baby marrows were present on the date of harvesting, while plants 2 and 3 produced fruit from a single application of Elementol B and water.

Plant 2: 64.95 g

Plant 3: 28.38 g

The study was not continued.

Study 2

Enhanced Uptake and/or Delivery of Nutrients in Hydroponically-cultivated Clivias The uptake of some of the minerals and trace elements from supplied hydroponic media is sometimes problematic. Study 1 showed in a very small number of plants that Elementol vesicles are taken up by plants and may even contribute to their growth. In study 2, a basic hydroponic nutrient mixture was entrapped in Elementol vesicles and growth of the plants was monitored.

Test Subjects:

5 groups of 6 Olivia seeds each were planted in wooden chips in carton plant holders. The groups were treated daily as described below:

Group 1 received 5 ml of $H_2O$

Group 2 received 5 ml of hydroponic medium diluted in $H_2O$ to the stipulated concentration Group 3 received 5 ml of hydroponic medium mixed with a low concentration Elementol B (1.98%) to the stipulated concentration Group 4 received 5 ml of hydroponic medium mixed with a high concentration Elementol B (4%) to the same concentration used in Groups 3 and 4

Group 5 received 5 ml of hydroponic medium diluted with nitrous oxide saturated $H_2O$ to the same concentrations used for the other groups.

Results:

Bulb Formation:

After 5 weeks bulbs were investigated with the following results:

Group 3 showed significant bulb formation with 2 of the seeds showing the formation of multiple bulbs from a single seed, whereas group 5 showed bulb formation but the bulbs seemed soft and slimy. Group 1 showed poor small bulb formation. Group 2 showed bulb formation, but bulbs weighed only 38% of the bulbs of group 3.

Vegetative Growth:

The vegetative growth was determined by measuring the length of the longest leaf of the plant after the indicated time periods, as indicated in FIGS. 11 and 12, which illustrate growth over time and a comparison of growth after 5 weeks. The growth of the 2 groups containing hydroponic nutrients dissolved in $H_2O$ or $N_2O$—$H_2O$ but no Elementol B are much on a par, with the leaves of group that received $N_2O$—$H_2O$ slightly longer than the plants that received water only. Of the groups that received hydroponic nutrients mixed with Elementol B, the group that received the low Elementol concentration showed the best growth of all groups, whereas the group that received the high Elementol concentration showed the worst growth. The plants were grown in carton plant holders and problems with drainage were clear from the mold growth in the wooden chips and on the cartons of plant holders that received the high Elementol concentration, as well as from the sliminess of the bulbs of this group. At this stage no conclusions can be drawn from this group. An Elementol dilution series will have to be investigated.

EXAMPLE 7

Use of Elementol R as Delivery Vehicle for Foliar Nutrient (Calcium) Administration on Strawberries Introduction:

The planting of the strawberries on the 12 ha trial plot commenced during early April 2005. The plant material is all first generation. The planted blocks slope down in a westerly direction and the elevation is roughly 100 meters above mean sea level. The soil has a clay content of less than 5% and an organic carbon content of 0.5%.

Trial:

This trial had the following as objective:

Spraying Elementol B and calcium as a foliar application, by tractor, to observe any reaction by the plants with regards to improved calcium levels in the leafs.

The experimental spray, per hectare, comprised of the following:

250 liters of water
250 ml of Elementolid
5 kg $CaCl_2$

Trial and Control:

The trial blocks were numbers 5, 6 & 7, whilst the control blocks were 1, 2, 3 & 4. The trial blocks were treated with the mentioned combination, whilst the control blocks were treated using a commercial "fulvic acid/$CaCl_2$" complex. The percentage calcium in both trial and control was the same.

Observations:

The leaf calcium levels in the trial blocks were determined 21 days after application and found to be as follows:

| Block | Pre treatment % Ca | Post treatment % Ca | % gain |
|---|---|---|---|
| 5 | 0.86 | 1.00 | 16.28 |
| 6 | 0.85 | 1.01 | 18.52 |
| 7 | 0.88 | 1.07 | 21.59 |

The leaf calcium levels in the control blocks were determined 21 days after application and found to be as follows:

| Block | Pre treatment % Ca | Post treatment % Ca | % loss |
|---|---|---|---|
| 1 | 0.86 | 0.85 | 1.16 |
| 2 | 1.15 | 0.84 | 26.95 |
| 3 | 1.08 | 0.80 | 25.93 |
| 4 | 1.03 | 0.84 | 18.45 |

Conclusion:

It is clear from the results that there is a definite improvement in the leaf calcium levels when $CaCl_2$, in combination with Elementol R is applied to strawberries.

EXAMPLE 8

Use of Elementol R in Foliar Administration to Determine Effects on Cherry Bell Peppers Introduction:

Planting was done on a 1.2 ha test plot using seedlings from the nursery. The plants were drip irrigated. Spacing within the row left the plants 300 mm apart, whilst the rows were double rows measuring 450 mm apart. Plant population per hectare was 30,000.

The fertilisation approach was to supply some 300 kg/ha of nitrogen, mainly in the form of calcium nitrate and potassium nitrate. The yield objective was 30 ton/ha. Flowering occurs during December and continues, while harvesting starts in late February and continues to the end of June. Prime picking is from mid March to mid May after which the volumes started to taper off. During peak picking 4 tons/ha may be harvested every 10 days.

Trial:

This trial had the following as objective:

Spraying Elementol R as a foliar application to observe the effect on "increased flowering" as well as early colouring towards the harvesting period. The experimental spray, per hectare, comprised of the following:

200 liters of water
200 ml of Elementol R

Control:

The control area comprised a small area on the same block and received no Elementol R.

Observations:

More flowers were observed in the trial compared to the control towards the end of December, but no counts were made.

Towards the end of January, fruit in the trial showed signs of advanced colouring compared to the control, but observation was made difficult due to high temperatures resulting in colouring on the control too. The feel is, however, that there was a better colouring on the trial compared to the control.

Conclusion:

It is unclear whether the Elementol did in actual fact contribute significantly to the advanced colouring of the cherry bells since other factors, such as the temperatures, fertilisation distribution, etc. may have influenced the result. The grower did however feel that there was a difference.

The real significance is that the grower yielded 29 ton/ha over the harvest period of which 24 ton were of commercial value. This yield is substantially better, compared to the area average.

Due to the grower's observations, he increased the application of Elementol R to 250 ml/ha for 4 consecutive weeks when plants start flowering with the following results:

Plants were larger with better leaf coverage;
The yield of fruit harvested was increased by 15% due to Elementol R administration;
The colouring of the Elementol-treated plants is "aggressive".

The grower found that at least 3 treatments were necessary before maximum impact of Elementol R was observed.

EXAMPLE 9

Use of Elementol B as Delivery Vehicle for Foliar Nutrient Administration on Sun Flower Introduction:

Planting was done in seedbeds measuring 910 mm apart (old 3 feet spacing). The plant population at planting was calculated at 40,000 seeds per hectare with an expected emergence of between 35,000 and 38,000 plants.

Action (Trial):

Two fields about 1 Km apart were involved, not because they were destined or prepared for a trial, but simply because they were in close proximity to each other and one could serve as a control for the other. The trial plot was about 95 ha in extent and the control plot about 200 ha.

The trial plants were sprayed with the following:
1 liter/ha "AminoPotas" (100 g/l "K" complexed or chelated with amino acid)
½ liter/ha "Aminocalcium" (100 g/l "Ca" complexed or chelated with amino acid)
5 kg/ha urea (2.3 kg "N" as NH4)
50 ml/ha Elementol B
27 liter/ha water The spray mixtures were made up in a mixing tank car and application was by aerial spraying.

Control:
The control was sprayed with the same mixture, excluding Elementol B.

Observations:
Measurements made to ascertain the difference in yield between the trial and control was done by the separate "weigh in" of the combine harvester's hopper (the bin into which the seed flows once separated from the flower bowl).

Conclusion:
The sampling result was as follows:
Trial: 2,735 kg/ha
Control: 1,650 kg/ha
Difference: 1,085 kg/ha
Average enhancement: 65.8%

EXAMPLE 10

Use of Elementol R in Degreening Apples

Elementol R was applied by hand spray at the start of fruit formation in a trial row of an orchard, while other rows in the orchard received no treatment. The Elementol R sprayed apples degreened substantially before the untreated apples.

Similar results were obtained with Cherry Bell peppers with aggressive colouring due to Elementol treatment. (4 applications) application rate 1 l/ha (see Example 8). What makes the colouring results of the apples, citrus and cherry bell pepper significant is the fact that these results show that the administration of Elementol R had the same impact on C3 and C4 plants, on annuals and perennials, on controlled environment and open field trials.

EXAMPLE 11

Effect of Elementol Foliar Application on Vines

Two vines in the same vineyard were selected to compare the effect of a single application of Elementol B to the whole vine, including the stems with handspray, but excluding the roots.

The diameter of the treated vine stems were significantly thickened and foliar index dramatically increased. The yield of fruit was also higher.

EXAMPLE 12

Fungal Protection by Elementol and Increase of Shelf Life of Roses with Elementol B Red Success roses known to be highly susceptible to white rust infestation were treated with Dithane made up and applied according to the manufacturer's specification. Trial plants were sprayed with similar Dithane formulations to which Elementol B was added to obtain a 1 in 10 dilution.

It was found that the Dithane/Elementol B treated plants had no sign of white rust when plants all around it became infected, and moreover seemed to last for a very long time after picking before it started wilting.

EXAMPLE 13

A Comparative Study of the Enhancement of the Efficacy of Round-Up by Elementol

Aim: The eradication of steenboksuring.
Weed: Steenboksuring, a hardy and stubborn weed that is nearly impossible to eradicate with any treatment.

Treatment:
Roundup Turbo was used as herbicide in the following manner. Reference control plots were treated and evaluated in the same manner as the treatment plots with respect to added herbicide and culturing practices. Various treatment plots were allocated. The treatment is described in more detail below.

Test Treatment:
A concentration of 0.6% Roundup Turbo and 40 ml Elementol B was diluted to 40l and applied to 1 ha. A field of 80 ha were sprayed with this mixture.

Reference Treatment:
Roundup Turbo was used as herbicide in the following manner: The herbicide was diluted to a final concentration of 2.8% of Roundup Turbo without the addition of Elementol B. A similar volume was applied per hectare to a similar acreage (80 ha).

Control plot: The treatment plots were set out in strips within a bigger field planted with Smutsvinger grass. The untreated areas of this field were used as control plot.

Method of Application:
The method of application was exactly the same for both test and reference treatment in terms of dosage rates and application equipment (nozzle with pressure). The herbicide was applied by spraying with tractor and spraying apparatus. The herbicide was applied once only, during the mid-winter. No wetting agent or adjuvant was added to either of the test or reference treatments Results and Observations:
a) One week after application, the grass or steenboksuring showed wilting in the test but not reference plants.
b) After two weeks, the test treated plants showed typical phytotoxic symptoms i.e. a yellowing of the leaves (chlorosis), which was followed by necrosis.
c) One and a half month after application, most of the steenboksuring showed severe phytotoxicity while all of the grasses were dead.
d) Observations reported include all variations, either inhibitory or stimulatory, between the treated and the untreated (control) plants.

Such variations may be formative (leaf and stem deformation) effects, and/or growth and development rates.

Conclusion
Despite using 79% less Roundup Turbo in the test treatment, the resultant death of the weed was enhanced in the presence of Elementol B.

EXAMPLE 14

A Comparative Study of the Enhancement of Apple Stool Beds and Nursery Trees by Elementol R (2005/2006)

Stool beds: This is a conglomerate of stems cultivated from a specific rootstock, examples of which are M7 or M9. The purpose of this cultivation is to produce a large quantity of "stems" onto which apple varieties of choice may be grafted. Such varieties may be Gala, Royal Gala, Brae burn, Oregon Red Spur etc. During such cultivation, success is measured by the amount of stems available for grafting from any conglomerate. Stem thickness is the main criteria whilst root quality and volume is secondary. Stems that are too thin do not allow for grafting.

Nursery trees: This is rootstock that has been grafted prior to being transplanted for initial growth. The ideal is to have these to grow to at least 1.5 meters in height before it is considered ready for commercial transplanting.

Trial Objective

The primary objective was to introduce Elementol R with the purpose to establish the effect it has on the improvement on stem thickness in a nursery environment. This effect was first noticed on randomly treated oak trees. The secondary objective was to enhance the growth of the grafted trees for commercial transplantation.

Method

The application method was as a foliar spray along with some foliar applied nutrient spray. 80 Stool beds were treated with 100 ml Elementol R/20 liter water, meaning 1.25 ml Elementol R was applied along with nutrients per stool bed. This application started during November 2005 and was repeated every 10 days. The programme was maintained until the present.

Control

The control stool beds received the same treatment except that no Elementol R was added.

Result

Results obtained during the first week of February 2006: The treated beds yielded 63/100 (63%) graftable stems, whilst the control yielded only 34/100 (34%). The average stem thickness was 11 mm.

Results obtained during the second week of February 2006: The trees grafted from rootstock stems that are on the Elementol R programme are on average 2 m tall, while those cultivated without Elementol are on average 1.5 m tall. The Elementol R treated trees have started to feather, i.e. side shoots have developed, whereas feathering is completely absent in the trees where Elementol R was not applied.

Cognizance must be taken that approximately 6 weeks of development remains for both control and trial. Though it is anticipated that the control may improve, it is unlikely to match the trial with Elementol R. Many variations of the invention may be devised without thereby departing from the spirit of the invention as formulated in the above statements of the invention.

EXAMPLE 15

A Comparative Study to Determine to Effect of Elementol R on the Germination of Hardscaled Seeds Arrow Leaf clover seed is known to be a hard scaled seed that lacks consistency in germination. The Elementol formulation according to the invention was shown to be beneficial with regards to the germination of these seeds by soaking quantities of the seed in clean water, undiluted Elementol R and in a 5% solution of Elementol in water for 24 and then packing the soaked seeds on seed beds, and observing the germination thereof. It was found that the seeds that had been soaked for 24 hours in the 5% solution of Elementol in water had a 30% better germination rate than the two other groups of seeds.

EXAMPLE 16

The Biostimulatory Effect of Elementol R: Effect of Elementol Foliar Administration on the Growth and Development of Lettuce 1. Material, Plant Growth and Treatment Plant: Lettuce or cos, romaine (*Lactuca sativa*) of the family: Asteraceae/Compositae (aster/daisy family).

Cultivar: Lettuce (*Lactuca sativa* L.), cultivar Red Poem, was used and was well established (approximately six weeks old) when purchased from a local nursery.

1.1 Culturing Method: Non-Circulating Hydroponic "Drip" System

PVC pipes with holes to fit the pots were used and connected to a reservoir and an aquarium pump to supply the plants with equal amounts of water and nutrients via the PVC pipe. Leaks were sealed to ensure that no water leaks from the system. A reservoir that contains the nutrient solutions were placed under the pipes and an aquarium pump supplied the plants with water and nutrients. The pump was connected to a timer to control the amount of water and nutrients supplied to the plants. The runoff was caught in a separate reservoir thus non-circulating the system and was discarded.

To control the amount of water for each plant, drippers were used to regulate pressure in the system and supply equal amounts of water (±9 ml four times a day) to each plant. The non-circulating drip system ensured that the plants received optimal water supply and the nutrient medium pH and EC (electrical conductivity) were constant. The EC of nutrients in the supplying reservoir as well as the runoff reservoir was measured, which enabled a determination of the amount of nutrients supplied versus the amount discarded. The amount of nutrients used by the plant or retained by the support medium can thus be calculated. Thus when the EC drops or increases too much, the nutrients could be added or retained from the nutrient solution supplied to the plants accordingly. A PW 9526 Digital Conductivity meter was used to measure the EC in milliSiemens per centimeter ($mS \cdot cm^{-1}$). Non-circulation of the nutrient medium may curb the spread of diseases in the system from infected plants to uninfected plants.

1.2 Growth Medium, Nutrients and Transplantation

Coconut fibre was used as support medium in the hydroponic system. It is an inert medium with the ability to retain enough water and air for good root development and good water retention.

A Hydrotech nutrient solution with the following composition was used: Macro elements: Nitrogen (N) 68 g/kg, Potassium (K) 208 g/kg, Phosphorous (P) 42 g/kg, Magnesium (Mg) 30 g/kg, Sulphur (S) 64 g/kg. Microelements: Iron (Fe) 1254 mg/kg, Copper (Cu) 22 mg/kg, Zinc (Zn) 149 mg/kg, Manganese (Mn) 299 mg/kg, Boron (B) 373 mg/kg and Molybdenum (Mo) 37 mg/kg.

Nutrients consisted of a mixture of Hygrotech nutrient solution and Calcium nitrate nutrient solution in equal amounts: 36 g of Hygrotech and 36 g of Calcium nitrate were dissolved in 2 L of water and then added to a reservoir containing 38 L of water. The pH and electrical conductivity of the nutrient solution are an indication of the dissolved ions present in the nutrient solutions and were monitored.

The lettuce were transplanted from the original containers into the hydroponic containers containing coconut fibre as well as course gravel in the bottom of the container to ensure adequate drainage of water and aeration to the roots. Before the lettuce was transplanted they were rinsed of any additional soil that might still be around the roots. The plants were weighed. After transplantation the plants were placed in the system and left to acclimatize for one week before experimentation began.

The plants were also placed in random order each week to ensure they receive equal amounts of sunlight, heat, water etc.

1.3 Glass House Conditions

The study was done inside a glass house to ensure optimum temperature as well as humidity levels to the plants in the hydroponic system. Most of the atmospheric conditions could be controlled effectively and the risk of diseases was minimized. The temperature of the glass house was measured on a weekly basis at twelve in the afternoon right above the hydroponic system with a thermograph.

The temperature in the glass house was regulated by an air conditioner. The temperature was regulated at maximum 24° C. and minimum 15. The maximum temperature was 28° C. and the lowest temperature was 4° C. The maximum and minimum temperature was obtained by using a thermohydrograph and both a daytime and night temperature was taken.

The relative humidity (RH) was measured by using a swirl thermohydrograph and both daytime and night time humidity was taken into consideration. The relative humidity could be determined in percentage of maximum humidity of the atmosphere, % RH. The highest RH % was 98% and the lowest RH % was 29% (26 Mar. 2006).

1.4 Light Intensity

Light intensity inside the glass house was measured with a Quantum/radio/photometer. Light intensity was determined at twelve daily right above the hydroponic system. Clouds and overcast conditions influenced the light intensity. The changing of the season also affected the light intensity. During the winter months the light intensity was lower than those taken during the warmer months. The maximum light intensity at 12h00 was 4600 $\mu E \cdot m^{-2} \, sec^{-1}$. The lowest light intensity at 12h00 was 850 $\mu E \cdot m^{-2} \, sec^{-1}$.

Care was taken to expose all plants to equal amounts of sunlight and other a-biotic factors. Plants were moved into different arrangements every week.

1.5 Plant Treatment

Control plants (C) received no treatment at all. Treatment with Elementol R as described above was prepared as follows:

3 ml Elementol R was mixed with 250 ml $H_2O$

Leaf treatment of the test plants consisted of spraying the Elementol R mix onto the leaves until saturation state but just before drip status. The plants were sprayed with spray bottles and care was taken not to contaminate the system or the support medium. The plants were treated every four weeks (week 1, 5 and 9) till the end of the study. For every two plants used as control, 3 plants were treated with the Elementol R mix. By treating two or more than two plants with the same treatment, a good average could be obtained per treatment.

1.6 Treatment of Diseases

Various diseases occur on lettuce. Fungal diseases were treated systemically with Funginex®. The plants were treated whenever fungal disease was noted by applying diluted Funginex® (3 ml of fungicide added to 500 ml of $H_2O$) onto the leaves.

2. Measurement of Growth and Development Related Parameters

Before transplantation of the young lettuce plants they were weighed and thereafter they were weighed weekly with a Mettler PJ 3000 balance. The weight of the non-plant material and pot was determined and was subtracted from the total mass to determine the plant weight after each week's growth.

2.1 Growth and Development

The growth of the lettuce heads were measured on a weekly basis. The average head diameter values were calculated from three diameter values. The plant height was measured from the top of the coconut fibre to the top of the tallest leaf. The average head diameter and height for each treatment was then calculated.

Figure 13:
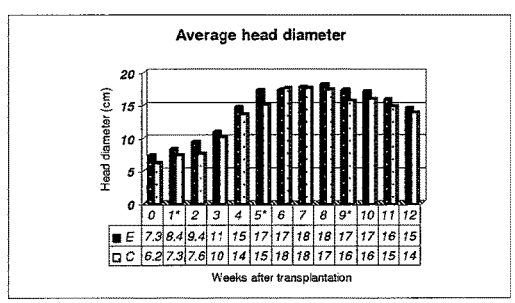
FIG. 13 is a graph showing the average head diameter of Elementol R-treated lettuce plants versus control plants over a 12 week period after transplantation as described in Example 16.

Treatment with Elementol enhanced the average growth of the plants as determined by head diameter by an average of 11% over the trial period (see FIG. 13 which is a graph showing the average head diameter of Elementol R-treated lettuce plants versus control plants over a 12 week period after transplantation.) The asterisks indicate the time of treatment. Three treatments with Elementol were given during the trial period.)

The % enhancement was calculated according to the following formula:

$$\% \text{ Enhancement} = \frac{ave \text{ head diameter of test plant} - ave \text{ head diameter of control plants}}{ave \text{ head diameter of control plants}} \times 100$$

Figure 14:
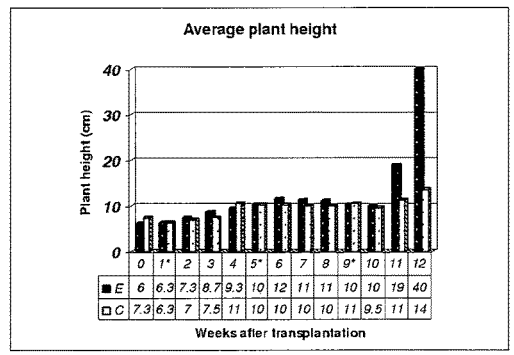
FIG. 14 is a graph showing the average comparative growth in plant height of Elementol R-treated lettuce plants versus control plants over a 12 week period after transplantation as described in Example 16.

The average comparative growth in plant height of the plants was very similar for the treated and control plants until week 11 when the plants reached maturity (See FIG. 14 which is a graph showing the average comparative growth in plant height of Elementol R-treated lettuce plants versus control plants over a 12 week period after transplantation.) Note the dramatic increase in growth in week 11. The enhancement in growth correlated with flowering—the Elementol R treated plants were the first to flower, suggesting that Elementol R might shorten development time.

Figure 15:
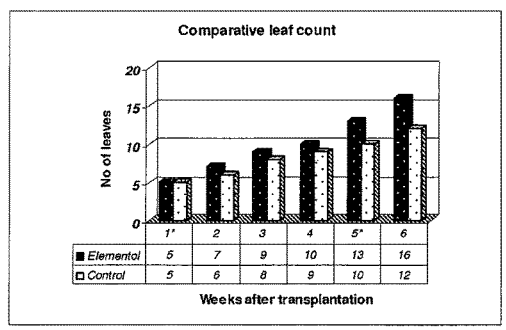
FIG. 15 is a graph showing an example of a plant by plant comparison of Elementol R-treated lettuce plants versus control plants as described in Example 16, using plants with a similar number of leaves at 1st treatment.

Another measurement of the enhancement of plant development is to compare the number of leaves of the treated and control plant (See FIG. 15 which is a graph showing a plant by plant comparison of Elementol R-treated lettuce plants versus control plants using plants with a similar number of leaves at 1st treatment.) The asterisks indicate the weeks of treatment (week 1 and 5.) The average enhancement over the 5 week period was calculated to be 20.7%.

2.2. Fresh and Dry Mass (Fm:Dm), Fm:Dm Ratio and % Water

This ratio indicates the amount of water and dry mass present for each gram of plant material. Dry mass is the amount of dry material left after all water has been removed and is an indication of the effectiveness of growth. The fresh and dry mass of the plants was measured every two weeks. To determine the fresh mass ten cylindrical disks of exactly the same size were cut from fresh leaves and the mass of each disc was determined. The disk was placed in a Labotec oven at 72° C. for 72 hours. The dry mass was then determined. The fresh mass to dry mass ratio was obtained by dividing the fresh mass by the dry mass.

Figure 16:
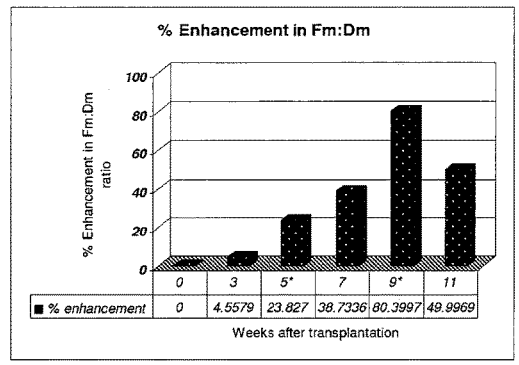
FIG. 16 is a graph that illustrates the average % enhancement in Fm:Dm ratios during the trial period caused by Elementol R-treatment of the lettuce plants versus control plants as described in Example 16.
Figure 17:
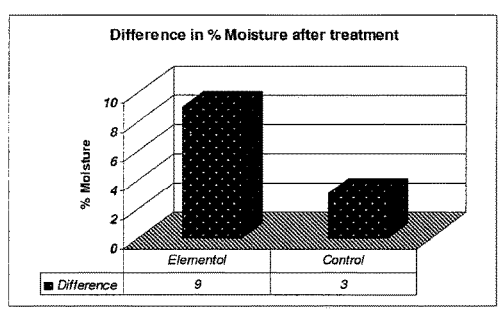
FIG. 17 is a graph that illustrates the difference in the Elementol R-treated lettuce plants and control plants in terms of the % moisture as described in Example 16.

The total average % enhancement in Fm:Dm ratios caused by Elementol R treatment over the trial period was calculated to be 39.5% (see FIG. 16 which is a graph that illustrates the average % enhancement in Fm:Dm ratios during the trial period caused by Elementol R-treatment of the lettuce plants versus control plants.) The total average % enhancement over the trial period was calculated to be 39.5%. See also FIG. 17 which is a graph that illustrates the difference in the Elementol R-treated lettuce plants and control plants in terms of the % moisture.

To determine the % of moisture in the leaves, the following calculation was used:

$$\% \text{ Moisture} = \frac{(\text{Fresh mass} - \text{Dry mass})}{\text{Fresh mass}} \times 100$$

The % moisture indicates the amount of water present in the plant. The amount of water present in lettuce must be in correlation with the dry mass of the lettuce. The moisture % was relatively stable during the period of the trial, although the % moisture of the Elementol-treated plants maintained a 5% moisture content during the last 6 weeks of the trial (week 8 to week 14), indicating that Elementol treatment results in some water retention ability. The higher moisture content is not sufficient to explain the much higher increase in Fm:Dm ratio.

3. Measurement of Physiological Related Parameters

Plant respiration, photosynthesis, chlorophyll, protein (12% SDS PAGE) and sugar content were used as physiological parameters. Besides reflecting the health of the plant, these parameters may give an indication of reason for the enhancement in growth and development by Elementol. Each of these parameters (except sugars) was determined once a week for all plants.

3.1 Protein Content

Protein was measured on a two weekly basis from week one onward according to the method described below. ±1 gram of fresh mass was taken weekly to determine the protein concentration of each plant. The fresh leaves were grounded in 5 cm³ mM Tris-HCl buffer (pH 6.8) containing 2 mM EDTA, 14 mM 6-2-Mercapto-etanol and 2 mM PMSF using a mortar and pestle. The crude extract was centrifuged on a cooled bench centrifuge for ten minutes at 12 000 rpm. The supernatant was removed and diluted 5 times. The protein concentration of the dilution was determined according to the Bio-Rad method of Bradford (1976). The absorbency of the dilution was determined at 595 nm with a Bio-Rad microplate reader with bovine gamma globulin as standard with a concentration of 0.5 mg/ml. By taking four readings per plant the protein concentration could be determined reasonably accurately.

The protein concentrations of the treated plants and controlled plants were determined weekly and showed no significant difference.

3.2 Respiration and Photosynthesis

The $O_2$ consumption rate for respiration as well as the rate of photosynthesis could be determined by means of pressure manometry, using a submersible differential Gilson respirometer. Readings, expressed in nmol $O_2$ per hour per gram of fresh mass, were taken every few minutes. This method was adapted from Stauffer (1972). A steady state of gas exchange method was followed. Respiration was measured in dark conditions, whilst both photosynthesis and respiration was measured in conditions of constant light intensity.

Ten leaf disks per plant were cut from fresh leaves with approximately 1.5 cm diameter. The disks were removed at random from random leaves to ensure well-representative results for each plant. The disks were weighed, then placed into a Warburg reaction vessel with 500 µl distilled $H_2O$. 300 µl 12% KOH was added to the centre well along with folded filter paper to enlarge the absorption area for $CO_2$ from the inter vessel atmosphere. KOH absorbs $CO_2$ to form bicarbonate and ensures that only the amount of $O_2$ consumption and synthesis is measured. Each vessel was attached to the apparatus and left to equilibrate in the dark for the required period. Equilibration took place while the machine was oscillating at 25° C. in a water bath. After equilibration the atmospheric and manomertric valves were closed to ensure an air tight system. Readings (R) were taken at pre-determined time intervals: $R_1$ is the manometer reading difference between 10 and 20 minutes in the dark. P&R is the manometric reading difference between 40 and 50 minutes in the light. $R_2$ is the manometric reading difference between 65 and 75 minutes in the dark. The manometric readings correspond with a change in gas volume, which equals the amount of $O_2$ consumed and synthesized. The rate of respiration and photosynthesis is obtained by: the following formulas:

Respiration:

$$\mu l \ O_2 \text{ conserved} \frac{O_2 R_1}{\text{Minutes } R_1} + \frac{O_2 R_2}{\text{Minutes } R_2} \div 2$$

Photosynthesis:

$$\mu l \ O_2 \text{ produced} = \frac{O_2 P \& R}{\text{Minutes } P \& R} + \frac{O_2 R_1}{\text{Minutes } R_1} + O_2 R_2 \text{Minutes } R_2 \div 2$$

The rate of µl $O_2$/minute was converted to:

$$\mu l \ O_2/h/g \ Fm \rightarrow (\Delta \ \mu l/\text{min} \times 60 \text{ minutes}) \div g \text{ Fresh mass}$$

The gas exchange values were corrected according to the method of Gregory and Purvis (1965) using the following equation:

$$X = \frac{\Delta Vg \times (T')(Pb - 3 - Pw)}{(T + 273)(P')}$$

Where:
X=Total volume of gas measured (mm³) at standard temperature and pressure (STP)
ΔVg=Volume change on respirometer
T'=Standard temperature, 273° K
T=Temperature of warm bath, 25° C.
Pb=Prevailing atmospheric pressure, mm Hg
Pw=Vapor pressure of water at the prevailing temperature at which the experiment was conducted
P'=Standard pressure, 760 mm Hg
If:

$$\frac{1 \ \mu l \text{ volume} \times 273[645 \text{ mm Hg}(BFN) - 3 - 23.756]}{(25° \text{ C.} + 273)(760)} =$$

$$\frac{273(618.244)}{(298)(760)} = 0.745234 \ \mu l \text{ at } 25° \text{ C.}$$

Thus 1 µl=0.745234 µl real volume in Bloemfontein (BFN).
[$O_2$] in atmosphere=±21%
1 mol $O_2$=22.414 dm³ (liter)
=22.414 liters (dm³)=1 mol $O_2$ If: 1 liter=0.0446149 mol $O_2$
At sea level 1 µl=0.0446149 µmol $O_2$
At BFN: 1 µl=0.745234 µl=0.0332485 µmol $O_2$
To convert µl $O_2$ to µmol $O_2$:

$$\mu l\ O_2/h/g\ Fm \rightarrow \Delta\ \mu l\ \mu l\ O_2/h/g\ Fm \times 0.0332485\ \mu mol\ O_2$$

Respiration and photosynthetic rates were determined every week and by applying the above mentioned formula, the values are corrected to compensate for difference in air pressures at sea level or at higher altitudes. The respiration and photosynthesis rates as well as the photosynthesis:respiration ratios were relatively constant and comparable over the 13 week period of this trial. However, when the respiration rate is corrected for the protein content, enhancement of the respiration rate are found in the Elementol treated plants.

The respiration and photosynthesis rate were measured and placed in correlation with each other. Photosynthesis rate must always exceed the respiration rate because the gain of carbon must exceed the usage of carbon or else there will be a net loss of carbons. The higher the photosynthesis:respiration ratio, the better the growth rate, as there is a higher net profit of carbon when ratios are high. The ratio was relatively constant over the 13 weeks of the trial.

Photosynthesis, like respiration, shows a "U" shape; when the lettuce was planted the plants were very green and had a high chlorophyll content. The rate of both photosynthesis and respiration was high during the initial growth period as the high metabolism of young plants also requires a high photosynthesis rate to supply the plant with adequate amounts of sugars which is respired. Photosynthesis and respiration then decreased after which photosynthesis rate increased again. Photosynthesis rate must always exceed than respiration rate to supply the plant with enough sugars for primary metabolism and to supply the plant with sugars during secondary metabolism as well as to store additional compounds for later usage. The photosynthesis rate increased during the last few weeks to accompany the rise in respiration rate. A higher photosynthesis is also due to more chlorophyll present in the last few weeks. Higher chlorophyll content results in better photosynthesis ability.

Figure 18:
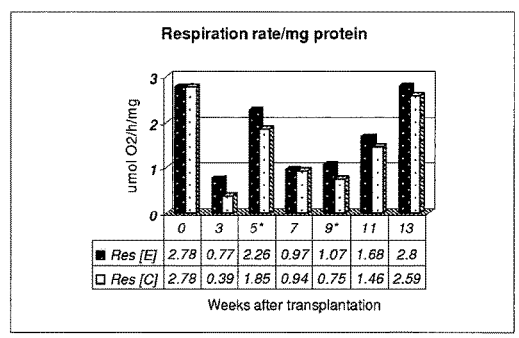
FIG. 18 is a graph that illustrates the respiration rate per mg protein for the study period in the Elementol R-treated lettuce plants and control plants as described in Example 16.

The respiration rate of the Elementol treated plants is generally slightly higher than that of the controls, but the differences are not statistically significant, except in week 5 directly after the second Elementol treatment (FIG. 18).

3.3 Chlorophyll Content

The synthesis of new living material requires an input of energy which is obtained from the sun through the process of photosynthesis. Chlorophyll is an essential component in photosynthesis. Chlorophyll is the main light absorbing pigment. Chlorophyll molecules are specifically arranged in and around pigment protein complexes called photosystems, which are embedded in the thylakoid membranes of chloroplasts. A few different forms of chlorophyll occur naturally, including chlorophyll a, chlorophyll b. Protecting pigments are also formed by many plants. Some of these accessory pigments, particularly the carotenoids, serve to absorb and dissipate excess light energy, or work as antioxidants. Other pigments such as caretenoids play a role in light absorption at different wavelengths.

The overall reaction of photosynthesis is shown in the following equation (producing one hexose sugar) (Stern, 2003).

$$6CO_2 + 12H_2O + light \xrightarrow{Chlorophyll} C_6H_{12}O_6 + 6O_2$$

During photosynthesis two light reactions are involved which include Photosystem I (PS I) and Photosystem II (PS II). These harvest light at different wavelengths for maximum efficiency. These two systems have to work co-operatively in order to be efficient. Systems can by light dependent or light independent. A major reaction during photosynthesis involves the transport of electrons from water to NADP, possibly through the mechanism known as the Z scheme. The rate of photosynthesis can be measured by determining the amount of carbon dioxide consumed or amount of oxygen released by using manometric techniques. Different types of photosynthesis occur and are termed $C_3$ photosynthesis (most plants), $C_4$ photosynthesis, most grasses, and CAM (Crassulacean Acid Metabolism) photosynthesis, which occur in most of the succulent plants. Factors influencing photosynthesis include light intensity and amount, availability of water, adaptation to sun and shady areas, availability of $CO_2$, temperature, leaf age, and carbohydrate translocation.

Chlorophyll content was determined weekly by using the extraction method of MacKinney (1941) by cutting 10 equal size disks at random from random leaves of the plant. The disks were grinded in 80% acetone in a mortar with a pestle on ice and the homogenate were centrifuged in a cooled bench centrifuge for 10 minutes at 12 000 rpm. The supernatant was diluted 5×. The absorbance values of each dilution were determined by using a Pye unicam SP8-400 uv/vis spectrophotometer. Absorbance values were measured at 663 nm as well as 645 nm in a 1 cm glass cuvette.

The concentrations of Chlorophylls were determined as follows (MacKinney (1941)):

$$\text{Chlorophyll } a\ (mg/g) = [12.7(A663) - 2.69(A645)] \times (V \div (1000 \times W))$$

$$\text{Chlorophyll } b\ (mg/g) = [22.9(A645) - 4.68(A663)] \times (V \div (1000 \times W))$$

Where: A=Absorbency of the dilution at the given wavelength
V=Final volume of extract
W=Fresh mass of disks used When a comparison is undertaken between the amount of chlorophyll in the experimental and control plants, one should correct for the amount of protein and fresh mass, as these has been shown to differ between the two groups.

Figure 19:
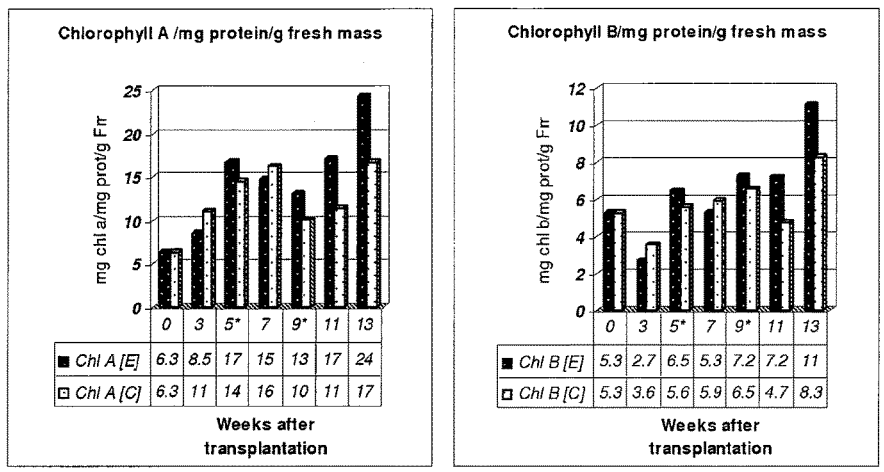
FIG. 19 are two graphs showing a comparison of the average chlorophyll A and B contents per mg of protein per fresh mass between Elementol R-treated lettuce plants and control plants for the period of the study as described in Example 16.

The Elementol R treated plants show an average increase in both chlorophyll a and b when compared to the control plants (FIG. 19).

Interestingly, the enhancement in especially chlorophyll a but to some extent also in chlorophyll b reflects a similar enhancement in Elementol-treated plants as that observed in plant height, number of leaves and amount of protein. An average enhancement of 14% and 20% over the total study period was observed for chlorophyll a and b respectively, while an average enhancement of 42% and 34% was observed during the last 4 weeks (week 9 to 13) of the study for chlorophyll a and b respectively. The combined results strongly suggest that the increase in chlorophyll content caused by Elementol treatment is directly responsible for the bio-stimulatory effect of Elementol R.

Figure 20:
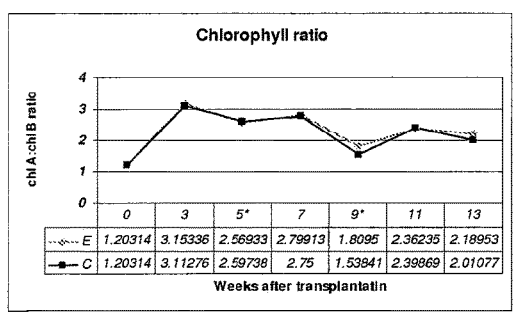
FIG. 20 is a graph that reflects the chlorophyll A:B ratios obtained from the chlorophyll corrected for mg of protein and fresh mass as described in Example 16.

Despite the difference in relative enhancement of chlorophyll A and B, a comparison between the corrected chlorophyll a to b ratios in the Elementol-treated and control plants showed no difference (see FIG. 20 which is a graph that reflects the chlorophyll A:B ratios obtained from the chlorophyll corrected for mg of protein and fresh mass. The nearly identical curves confirm the absence of any phytotoxic effect on the photosynthesis apparatuses of the plants.).

3.4 Sugars Content

The amount of sugar present is a direct result of the amount of nutrients available. Increasing the N and P rates gradually increased glucose content in lettuce but decreased the shelf life (www.ars.usda.gov). The respiration rate as well as photosynthesis rate has an effect on the amount of available sugars. The UV method of Boehringer Mannheim (Kit nr. 10 716 260 035) was used to determine sucrose, fructose and glucose concentrations present in lettuce leaves. Sucrose is present in much higher concentrations than glucose. A statistically significant but small increase in the amount of sucrose was found in control plants compared to Elementol R treated plants. Glucose on the other hand was slightly higher in the treated than in the control plants.

3.5 Brix

Plant phloem sap contains many substances which supply the plant with energy. One of the terms used in reference to quality is called Brix index and this concept was introduced by a 19$^{th}$ century German chemist, A.F.W. Brix. The Brix value is a measure of the percent soluble solids content (SSC) in a solution. Although Brix is often expressed as the percentage of sucrose, it is important to realise that the "sucrose" here is actually a summation of sucrose, fructose, vitamins, amino acids, protein, hormones and other solids (www1.agric.gov.ab.ca). The main storage form of carbohydrates in plants, namely starch, is insoluble and therefore does not contribute directly to the Brix value.

Each degree of Brix is equivalent to 1 gram of sugar and other SSC per 100 grams of juice. Generally, the higher the Brix, the higher sugar content, especially increased sucrose and glucose levels (Baxter et al., 2005) and this normally results in better taste (Baxter et al., 2005; www1.agric.gov.ab.ca). High Brix, high EC and low pH are generally associated with high fruit quality (www.cals.ncs-u.edu).

When a crop is cultivated under favourable conditions, such as hydroponic systems where there is unlimited supply of minerals and other required nutrients, sufficient sunlight and temperature, a higher Brix in the plants can be expected in those produce (www1.agric.gov.ab.ca). Bisogni et al. (1976) found correlation between SSC and sweetness, flavour and overall quality. Winsor (1966) reported that the best quality of fruit were those high in both sugars and organic acids. (www1.agric.gov.ab.ca).

Brix equals the % dissolved solids in the phloem sap. A high Brix sap has a reduced water activity, with a corresponding reduction in freezing point, as well as a proportionally greater tendency to retain moisture.

Produce with higher Brix also have a longer shelf life, and are more resistant to pest infestation and disease. While temperature, pH, etc can influence if and how fast organisms will grow, water activity may be the most important factor.

Water Activity is thus a critical factor in determining shelf life as well as field success. Brix sap levels in excess of 12% also generally ensure against sap-sucking insect infestations.

Most importantly, high Brix provides proportionally greater nutritional content of the food and ensures good, true nature-ripened flavour, especially where the refractometer shows a diffuse or spread reading, indicating a variety of complex dissolved plant proteins and flavour components in good measure.

Brix is often used to determine the quality of some selected foods. Brix readings are readings of all dissolved substances present in the lettuce leaf and not only the sugar or sucrose content. Brix is in fact used to determine quality of lettuce The Brix refractometer was calibrated at room temperature using a 10% sucrose solution with a Brix reading of 1.3475. Neutralized $HClO_4$ was used as standard. The reading was subtracted from the Brix reading as well as the % sugars. After calibration a sample was placed in the refractometer and the Brix readings were taken in Brix readings as well as % sugar.

Another method was used to determine the Brix reading. ±0.1 grams of fresh mass were grounded in 200 µl water (Thus the sample was diluted 4×) and 20 µl of sample was placed on the refractometer and the Brix readings were taken.

Despite the lower sucrose content, the Brix values indicate a better quality lettuce obtained from the Elementol treated plants. Since Brix reflects the insolubles in the lettuce, the Elementol-treated lettuces are enriched in plant material other than sucrose. The % enhancement in Brix by Elementol treatment obtained with the $HClO_4$ method was 15% and that with the water method 12%. The 3% difference obtained with these two methods should be the due to a higher presence of organic acids, hormones or oil-based vitamins, as those are soluble in $HClO_4$.

EXAMPLE 17

The Biostimulatory Effect of Elementol R Administration on the Yield and Quality of Fruit in a Controlled Environment 1. Material, Plant Growth and Treatment Cultivar: Tomato *Lycopersicon esculentum* Mill of the family: Solanaceae cv.

Seedlings: Floradade seedlings, approximately six to eight weeks old, were purchased from a local nursery in Bloemfontein. Twelve of these seedlings were transplanted to the prepared hydroponic system in the glasshouse. This glasshouse was situated on the roof of the Plant Science building of the University of the Free State.

1.1. Culturing Method:

Two identical recycling ebb and flow hydroponic systems were set up. Each system consisted of 2 rectangular asbestos trays (90 cm×20 cm), filled with the support medium which consisted of disinfected, medium size, silica gravel. Three seedlings per tray were transplanted ±30 cm apart and rows ±42 cm apart. This spacing allows ±0.135 $cm^2$ per plant, resulting in 9 plants/1.22 $m^2$ In order to limit algae and bacterial growth, black non-translucent PVC piping, fittings and reservoirs were used to construct the recycling systems. Each system had a separate 70 liter reservoir, with a small water pump inside. Both these pumps were connected to a single digital timer, which regulated the intervals of watering cycles. The watering time was synchronized in order that the trays were filled up to a specific level, where after the timer switches off, and the water drained into the reservoir. The plants were flooded six times a day for 5 minutes, ranging from 06:00 to 18:00.

1.2 Greenhouse Conditions

The temperature in the greenhouse was partially controlled by an air conditioner. Average night and day temperatures ranged from 16° C. to 25° C., respectively. Three instruments, namely a thermometer, thermohygrograph and a swirl hygrometer, were used to determine the temperature. The thermometer was mounted on the eastern wall (facing north). The thermohygrograph was placed strategically inside the greenhouse to provide a 24 h record of the greenhouse conditions from Monday to Friday. The thermohygrograph provide an indication of both the temperature as well as the relative humidity. The light intensity of three different locations was measured with an LI-185A model photometer on a height of 2 m from floor level. Light intensity varies considerably with latitude and time of the year. This is a result of the inclination of the earth and rotation around the sun. Mid-day light intensity (LI) decreased as the winter months approached, followed by an increase from the $14^{th}$ week after transplant (WAT) until termination in the $25^{th}$ WAT.

The temperature, relative humidity and the irradiance intensity were measured following the same procedure as the weekly measurements. The readings were taken every two hours from 8:00 to 16:00 for one day during May and July. The relative humidity (RH) is the ratio between the weight of moisture actually present in the air and the total moisture-holding capacity of a unit volume of air at a specific temperature and pressure (Smith & Bartok, 2006). The mid-day RH initially increased to 82%, but from the $18^{th}$ week after transplantation, a drop to as low as 50% is noticed ($24^{th}$ WA). RH is temperature dependant, seeing that warm air has a higher moisture-holding capacity than cooler air; therefore as the temperature of air increases, the relative humidity decreases even though the amount of water remains constant. However, in this case the temperature remains relatively constant; therefore the drop in RH might be a result of vigorous growth of the plants, resulting in dense and high transpiration until commencement of the harvesting period. The growing vigour and transpiration rate ceases naturally as the harvesting period comes to an end.

1.2. Nutrient Solution

The nutrient solution applied, namely Hygrotech Hygroponic, is an optimized mixture of nutrients specifically developed for hydroponic tomato production. This mixture initially consisted of Hygroponic Mix and calcium nitrate. Potassium nitrate was added from third flower truss to the end the trial. The combination of the prescribed concentration of each component was dissolved in tap water.

The reservoirs were filled with 70 liters of nutrient solution and replenished as necessary. Every alternating week, before refilling, the reservoirs were flushed with clean tap water to dispose with any harmful substances that might have accumulated. The pH and EC of the nutrient solution in each reservoir were measured before and after refilling the reservoirs, using a PHM 85 Precision pH meter and a PW 9526 digital conductivity meter respectively.

2.1.3. Treatments

During the second WAT, the plants were raked up with black nylon twine in order to support the plants. During the $2^{nd}$ week, the first of six applications of applicable treatments were applied. The treatments are summarized below:

| Treatment | Abbreviation | Treatment composition |
|---|---|---|
| Control | C | no application |
| Elementol R | P | 3 ml Elementol R/250 ml H2O (2xdist) |

The plants were specifically arranged in an effort to have both sun and shade plants for each treatment. The only differentiation between plants was therefore the particular foliar treatment.

2. Physical Parameters: Growth, Development and Yield of Plants 2.1 Plant Height The height of each plant (from the level of gravel to highest tip) was determined with a measuring tape. As soon as the plants reached the roof and the weight of the plant pulled the plants down, this procedure were ended.

Plants of both treatments showed a linear increase in height, with an average height for both the treated and control plants ranging between 130 and 160 cm in week 10 after transplantation.

2.2 Regenerative Development

The impact of Elementol R on the yield of plants was evaluated firstly by counting the number of flower buds on the plants. The development and growth of plants are directly related to the formation of flower buds, flowers and fruit. Flower buds were recorded as soon as a clearly distinguishable flower bud appears, and flowers when a definite yellow colour is apparent. The first flower buds appeared three weeks after transplant to reach an average of approximately 25 buds for Control (C) plants at 7 weeks after transplantation.

Figure 21:
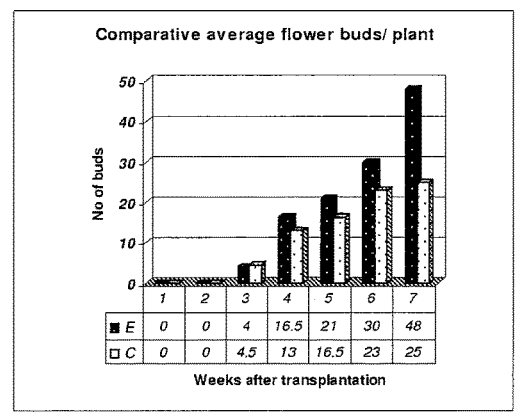
FIG. 21 is a graph showing the changes in average number of flower buds formed during the first few weeks after transplantation (WAT) in Elementol R treated and control tomato plants as described in Example 17.

Although Elementol R (Er) treatments had no statistically significant effect on plant height, treatment with Elementol R resulted in a statistically significant increase in average number of flower buds, especially between $5^{th}$ and $7^{th}$ week after transplant (FIG. 21).

Figure 22:
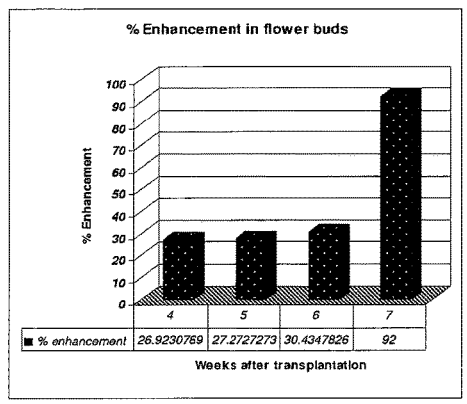
FIG. 22 is a graph showing the average % enhancement in flower bud production of Elementol R treated and control tomato plants as described in Example 17.

Compared to Control plants, the Elementol R treatment stimulated bud formation significantly as from week 6. The % enhancement was calculated according to the formula described in Example 16, with an enhancement of 92% recorded, with an average enhancement in flower buds of 44% from week 4, when clearly distinguishable flower buds could be counted, to week 7 (table 1 below and FIG. 22).

TABLE 1

| Average flower buds | | | |
|---|---|---|---|
| WAT | Er | C | % enhancement |
| 4 | 16.5 | 13 | 26.92308 |
| 5 | 21 | 16.5 | 27.27273 |
| 6 | 30 | 23 | 30.43478 |
| 7 | 48 | 25 | 92 |
| Average % enhancement week 4-7 | | | 44.15765 |

To prevent damage to developing plants, and impracticality of bud counting in densely populated hydroponics setup, it was decided to terminate this procedure 7 weeks after transplant.

2.3 Yield

Figure 23:
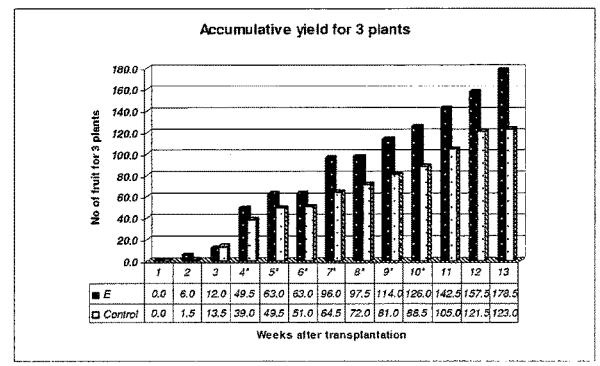
FIG. 23 is a graph that shows the linear increase of accumulative average yield for 3 tomato plants over the period of the study as described in Example 17.

The contribution of Elementol R to yield could not be determined in Example 16, where leaf and plant growth were the relevant parameters. In the case of the tomato plants however, an enhancement in flower buds should reflect an enhancement in the yield of plants, if the nutrition given to the plants hydroponically is sufficient. The fruit was therefore counted. Fruit needed to reach 5 mm in diameter before its appearance was recorded. The average accumulative yield of fruit during the study period is recorded in table 2 (see also FIG. 23).

TABLE 2

| Average accumulative yield (total n) | | |
|---|---|---|
| WOH | Control | E |
| 1 | 0.0 | 0.0 |
| 2 | 1.5 | 6.0 |
| 3 | 13.5 | 12.0 |
| 4* | 39.0 | 49.5 |

TABLE 2-continued

Average accumulative yield (total n)

| WOH | Control | E |
|---|---|---|
| 5* | 49.5 | 63.0 |
| 6* | 51.0 | 63.0 |
| 7* | 64.5 | 96.0 |
| 8* | 72.0 | 97.5 |
| 9* | 81.0 | 114.0 |
| 10* | 88.5 | 126.0 |
| 11 | 105.0 | 142.5 |
| 12 | 121.5 | 157.5 |
| 13 | 123.0 | 178.5 |

The weekly increase in yield for both the control and treated plants is linear from week 3, with a lag phase from transplantation to week 3. The Fisher t-test (1 tailed), which returns the probability associated with a Student's t-Test and determines whether two samples are likely to have come from the same two underlying populations, was used to analyse the yield data. The probability value was determined as 0.000261, meaning that the probability that the yield series obtained for the Elementol R treated fruit and control fruit is the same is less than 1 in a 1000.

The average enhancement in yield calculated over the period of the study, excluding week 1, again using the formula described in example 1, was 53.7%.

The average accumulative yield per plant was calculated. As expected, the % enhancement in fruit yield per plant was exactly equal to that obtained for total accumulative yield (53.7%).

Figure 24:
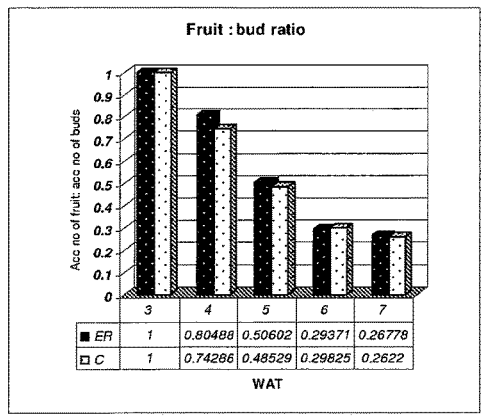
FIG. 24 is a graph that shows the average accumulative fruit to average accumulative bud ratio of tomato plants treated as described in Example 17.

A calculation of the fruit to bud ratios for both groups (table 3) show a progressive but similar decrease over the first 7 weeks, after which bud counting was terminated. In week 7, only 26 or 26 fruit are grown from every 100 buds (see FIG. 24). Thus is probably due to insufficient nutrition for both groups in view of the high yields obtained, despite the use of a nutrient mix optimized for hydroponically grown tomatoes. The higher the yield, the greater would be the impact of insufficient nutrition. Therefore a greater enhancement in yield of Elementol R treated plants compared to control plants could probably have been obtained if the nutrition were to have been adjusted to the increased yield.

2.4. Physical Parameters of Fruit 2.4.1. Moisture Content

Both total fruit yield and soluble solids content plays and important role in the economic success in the processed tomatoes market. For choice of tomatoes for processing purposes, specific attention is paid to biochemical quality. Fruit with high soluble solids content, for example, contain less water and are sweeter and consequently require less processing and addition of sugar to prepare pastes of proper texture (Baxter et al., 2005). In addition, a number of organoleptic and nutritional parameters are be used to define fruit quality. These quality parameters include sugars, titratable acidity (TA), electrical conductivity (EC), vitamin C and phenolic compound content, soluble solid content (SSC) and firmness, to name but a few (Anza, Riga & Garbisu, 2006).

Figure 25:
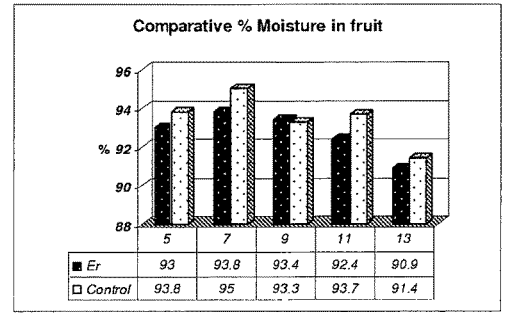
FIG. 25 is a graph that shows the average % of moisture found in the fruit of Elementol R treated tomato plants versus control plants as described in Example 17.

The average moisture content would thus give an indication as to the quality of the tomato. To determine the moisture content, a slice of each representative tomato fruit was placed in a Petri dish (of which the weight was pre-determined) and weighed by means of a Sauter RL 200 microscale. It was then placed into a labotech oven at ±68° C. for 7 days. After the dehydration period, the Petri dish containing the tomato slice was weighed again. The loss in weight represents the amount moisture present in the tomato. On average, the Elementol R treated fruit contains slightly less moisture than the control group although the difference is not statistically significant (see FIG. 25 which shows the average % of moisture found in the fruit of Elementol R treated tomato plants versus control plants as described in Example 17. Elementol R treated fruit generally had a lower moisture content relative to total tomato mass, indicating a fruit with more insolubles, such as sugars and protein, resulting in tomatoes of higher quality.)

The average % enhancement of dry mass (Dm) of Elementol treated fruit is −1.05% over the study period, indicating that no difference exist between the treated and control plants. However, the comparative dry mass has a wide distribution. The T-test of probability that the two ranges originated from the same group (i.e. similarity) was calculated as 0.330525. A reverse pattern is observed when the moisture mass: Dm ratios are compared. This may indicate that the procedure used for this determination is not accurate. A possible cause is that the organic acid and oil content of the fruit is not taken into account.

3. Biochemical Parameters of Fruit 3.1. Electrical Conductivity (EC) and pH

Every second week, 15 fruit, representative of each treatment, were objectively selected. A part of the fruit was ground up in a test tube using a Polytron Homogenizer. The pH and EC of the tissue were determined, by means of a PHM 85 Precision pH meter and the PW 9526 digital conductivity meter, respectively.

A greater flow in electrical current implies a higher concentration of dissolved ions in the fruit. Both total fruit yield and soluble solids content plays and important role in the economic success in the processed tomatoes market. For choice of tomatoes for processing purposes, specific attention is paid to biochemical quality. Fruit with high soluble solids content, for example, contain less water and are sweeter and consequently require less processing and addition of sugar to prepare pastes of proper texture (Baxter et al., 2005).

The EC of the fruit showed a progressive increase. The average EC determined for control plants over the study period was 3.395, while that for the Elementol R treated plants was 3.393. An inverse relationship, although it be with a very moderate slope, are evident when the relation between pH and EC values of the fruit are compared.

The average pH of the control fruit for the period of the study was determined to be 4.245, while a pH of 4.248 was found for the fruit of the Elementol R treated plants. Therefore, despite the greatly enhanced yield of the treated plants, no difference in the quality of the fruit in terms of moisture, dry mass, EC or pH. The close correlation in values also indicates the accuracy of the measurements.

3.2. Carbohydrates

The fruit quality and yield of tomatoes are largely determined by one of the biochemical components of fruit quality, namely the amount of soluble sugar content (Damon et al., 1988; Islam et al., 1996). The glucose and fructose concentrations in the apoplast are present in a ratio of approximately 1:1 (Damon et al., 1988), with the hexose concentrations at least four times greater than the sucrose at all stages of development. Guan and Janes (1991) found that sucrose levels are relatively low in tomato fruit, are independent of light intensity and that it continues to decline during development. The sucrose content of light- and dark-grown fruit in their studies did not shown any significant differences. The accumulation of carbohydrates may therefore be driven by the metabolism of sucrose.

Preparation of samples for assaying the carbohydrate content of the harvested tomatoes: Samples were prepared by adding 10 g of representative fruit tissue to 5 ml twice distilled water in a test tube. This mixture was homogenised for ±30 seconds with a Polytron Homogeniser. The remaining material on the side of the test tube was rinsed into the test tube with an additional 2 ml of twice distilled $H_2O$. The test tube was shaken for 30 minutes, followed by vigorous Vortexing, and then quickly poured into a small measuring cup. While the puree was being stirred on an electronic stirrer, the pH was adjusted to ±8.00 by using 1M and 5M KOH, where after the solution (±13-17 ml) was made up to a final volume of 20 ml. An aliquot (±1.5 ml in microfuge tubes) of the solution was centrifuged at 12 000 rpm for 10 minutes. The supernatant was collected with a Pasteur pipette and transferred to a clean tube. Assay samples were stored at −20° C. until final analysis.

To determine the sugar content of the fruit, the Sucrose/D-Glucose/D-Fructose—kit (10 716 260 035), manufactured by Boehringer Mannheim/R—Biopharm was used. The prescribed procedure was adapted to 1 ml volumes. Dilution factors were taken into account when calculating the carbohydrate content.

Table 3 shows the comparative glucose, fructose and sucrose content for the harvested fruit in week 13 of the study.

TABLE 3

| Comparative sugar content | | |
|---|---|---|
| mg/Fm | Elementol R | Control |
| Glucose | 13.73 | 13.52 |
| Fructose | 14.45 | 13.32 |
| Sucrose | 30.11 | 28.04 |

The Elementol R-treated tomatoes showed a considerable increase in fructose and sucrose content, resulting in sweeter tomatoes, which are preferred by the consumer.

3.3 Brix

The Brix value is an indication of the percent total soluble solids (TSS) in the fruit juice. Every second week, the Brix value of the same puree of the 15 representative fruit used for pH and EC, were determined. The procedure of grounding up a part of the fruit in a test tube using a Polytron Homogenizer, are therefore exactly the same as for determination of pH and EC of the fruit. The puree container was then slightly tilted in order to collect a clear juice sample with a pasteur pipette. The Brix value was determined by means of a refractometer. High Brix, high EC and low pH are associated with high quality (www.cals.ncsu.edu). Despite the fact that no statistical difference between control tomatoes and Elementol treated fruit was observed with regards to EC and low pH or moisture content of the fruit observed during the $13^{th}$ week of harvest, fruit from Elementol treated plants with an average Brix value of 8% outperformed the control plant, that had an average Brix value of 7.4%. Both of the groups had a significantly higher Brix value than the average published value for tomato.

In conclusion, Elementol R treatment enhanced both the yield of tomatoes as well as the quality of the harvested fruit in terms of % moisture, insolubles and sugars.

EXAMPLE 18

Enhancement of Uptake and Translocation of a Commercial Bio-Stimulant by Means of Elementol R 1. The Aim of this Study The previous two examples showed that Elementol R on its own can act as a bio-stimulant in terms of plant growth and yield. This study investigates whether the pre-entrapment of a commercial bio-stimulant, ComCat®, into Elementol R can enhance the uptake and translocation of this bio-stimulant, resulting in an increase in plant growth and yield beyond that observed with Elementol R or the known slight effect of ComCat®, on hydroponically grown lettuce and tomatoes.

2. Experimental Set-up:

The experimental set-up was similar to that described in Example 16 and 17, except that the bio-stimulant (alone and in combination with Elementol R) was administered. The study was executed in a similar fashion to those described in Examples 16 and 17 and will not be described again.

2.1 the Commercial Biostimulant ComCat®

ComCat®, an eco-friendly plant strengthening agent, contains one of a group of phytohormones, called brassinosteriods (Schnabl, et al., 2001). Brassinosteroids is a growth-promoting steroid found in higher plants. Brassinosteroids are thought to act at low concentrations to affect the growth of plants, by enhancing the elongation of stems and regulating gene expression in plants. Improved seedling development, strong roots and shoots, optimum flower development have been observed with the use ComCat®. Brassinosteroids, as pure phytohormones, have been reported to not only increase crop yields but also crop quality (Prusakova et al., 1999). ComCat® contains high-quality, biochemical active substances which have been extracted from synecologically active wild plants.

Due to interference from cultivators most cultivated plants have lost access to defend themselves against pathogens. ComCat® increases the resistance of plants to all types of stress and pathogens. Brassinosteroids play a decisive part in activating the plant's own resistance and tolerance mechanisms. ComCat® is the first of its kind to have succeeded in catalyzing this activation of the plant's own ability of defence in an optimum way. Plants develop induced resistance that increases the plant's ability to resist pathogens.

This bio-stimulant is a water-soluble powder, and when applied to crops as a foliar spray or a seed treatment, it increases root development, accelerates nutrient absorption, intensifies nutrient assimilation, induces flower bud formation, increases yields (Hüster, 1999, Schnabl et al., 2001, Pretorius quoted by Alam, 2004) and induces the natural resistance of plants against pathogens and biotic stress (Agra Forum as quoted by Alam, 2004; Huster, 1999; Schnabl et al., 2001). Khripach et al. (2000) also claimed that this newly discovered phytohormone has the ability to regulate the uptake of ions into the plant cell.

2.2 Foliar Administration Schedule 2.2.1 Lettuce

The treatments for the different groups of plants were prepared as follows:

According to ComCat® dosage directions: ComCat®=2 g/L

Thus: =0.5 g/250 ml i) ComCat® (CC)

0.5 g CC+250 ml $H_2O$ ii) Elementol R (E)
3 ml E+250 ml H$_2$O
iii) Full strength ComCat® and Elementol combination (CC/E)
0.5 g CC+3 ml E+250 ml H$_2$O
iv) Half strength ComCat® and Elementol combination (½CC/E)
0.25 g CC+3 ml E+250 ml H$_2$O
v) Quarter strength ComCat® and Elementol combination (¼CC/E)
0.125 g CC+3 ml E+250 ml H$_2$O 2.2.2. Tomatoes

| Treatment name | Abbreviation | Treatment composition |
|---|---|---|
| Elementol R | PE | 3 ml Elementol R/250 ml H$_2$O (2xdist) |
| ComCat | CC | 0.5 g Comcat/250 ml H$_2$O (2xdist) |
| ComCat & Elementol | CC/E | 0.5 g Comcat + 3 ml Elementol R/250 ml H$_2$O (2xdist) |
| 0.5 Comcat& Elementol R | 0.5 CC/E | 0.25 g Comcat + 3 ml Elementol R/250 ml H$_2$O (2xdist) |

3. Results
3.1 Growth and Development and Head Diameter
3.1.1. Lettuce

Pre-entrapment of CC in E did not greatly influence plant head diameter of plant height. Some of the plants did not increase 100% which means that they did not double in size. Some plants that were treated with CC and E individually performed the best of the treated plants but differences were not statistically significant, except from week 11 onwards, when Elementol R treated plants outperformed all other treatments. Some of these combinations may have an inhibitory effect on the plants, whereas E and CC individually both had a stimulatory effect.

The plants reached a maximal head diameter during the first 7 to 8 weeks, after which the head diameter decreases, probably because the plants were constantly pruned to obtain leaf material to do physiological experiments.

3.1.2 Tomatoes

ComCat® application resulted in a slightly reduced growth rate. However, when ComCat® is applied together with Elementol of either concentration (CC/E and 0.5CC/E), this reduction in vegetative growth is alleviated in a dose-dependent fashion, but growth is still significantly below that of Elementol R alone.

3.2 Average Flower Buds of Tomatoes

Elementol R alone, as well as ComCat® (CC), and combination treatments showed a marked increase in flower buds, especially between 5$^{th}$ and 7$^{th}$ week after transplant. No clear difference was measured between these treatments, although CC showed the least increase.

3.3 Average Tomato Yield

No clear differences were observable for fruit size and mass between all treatments. ComCat® (CC) application failed, as bio-stimulant, to enhance both fruit size and mass in hydroponically grown tomatoes. Full strength ComCom® with Elementol R application had no effect on changes in fruit size and mass, but CC/E combination application resulted in higher fruit size and individual fruit diameter and fresh mass (see 3.2.2 below). This suggests that this low ComCat®/Elementol concentration decelerate the decrease in fruit mass observed for the whole harvesting period which implies better physical yield for harvesting period. The table below reflects the average yield/plant:

| Average no of fruit/plant | | | |
|---|---|---|---|
| Control Avg | E Avg | CC Avg | CC/E Avg |
| 0.0 | 0.0 | 0.0 | 0.0 |
| 0.5 | 2.0 | 0.5 | 1.7 |
| 4.5 | 4.0 | 2.0 | 5.0 |
| 13.0 | 16.5 | 6.5 | 15.3 |
| 16.5 | 21.0 | 12.5 | 27.0 |
| 17.0 | 21.0 | 12.5 | 28.7 |
| 21.5 | 32.0 | 23.5 | 39.3 |
| 24.0 | 32.5 | 24.5 | 43.7 |
| 27.0 | 38.0 | 29.0 | 55.0 |
| 29.5 | 42.0 | 30.0 | 59.7 |
| 35.0 | 47.5 | 33.0 | 64.7 |
| 40.5 | 52.5 | 35.0 | 73.3 |
| 41.0 | 59.5 | 37.0 | 78.0 |

Elementol R stimulated the yield of tomatoes significantly (Example 17). However, when ComCat® is mixed with Pheroids, both in full (CC/E) and half (0.5CC/E) strength markedly stimulated fruit production (See FIG. 26 which is a graph that shows the effect of ComCat® (CC), Elementol R (E) and combinations thereof on changes in accumulative number of fruit harvested from 3 plants per group over a period of 13 weeks) and subsequent mass of fruit harvested (see FIG. 27 which is a graph that shows a dramatic increase in total accumulative fruit mass observed when plants are treated with ComCat® that is entrapped in Elementol R as compared to the increase observed with Elementol R or ComCat® individually.).

| Yield in terms of total fruit mass (avg acc mass/plant) | | | | |
|---|---|---|---|---|
| WOH | Control | P | CC | CC/P |
| 1 | Avg | Avg | Avg | Avg |
| 2 | 0 | 0 | 0 | 0 |
| 3 | 61.0 | 156.2 | 90.5 | 115.5 |
| 4 | 459.1 | 315.3 | 250.1 | 518.5 |
| 5 | 1083.4 | 1093.9 | 639.9 | 1424.9 |
| 6 | 1329.9 | 1331.4 | 974.8 | 2137.5 |
| 7 | 1361.0 | 1331.4 | 974.8 | 2221.6 |
| 8 | 1608.7 | 1888.7 | 1669.7 | 2844.7 |
| 9 | 1758.4 | 1928.6 | 1704.9 | 3092.5 |
| 10 | 1925.9 | 2152.9 | 1977.7 | 3808.5 |
| 11 | 2072.0 | 2261.9 | 2014.1 | 4109.5 |
| 12 | 2337.1 | 2498.0 | 2121.4 | 4385.5 |
| 13 | 2562.9 | 2682.0 | 2260.5 | 4818.5 |
| Average | 2589.1 | 2908.5 | 2358.2 | 5041.2 |

Figure 26:
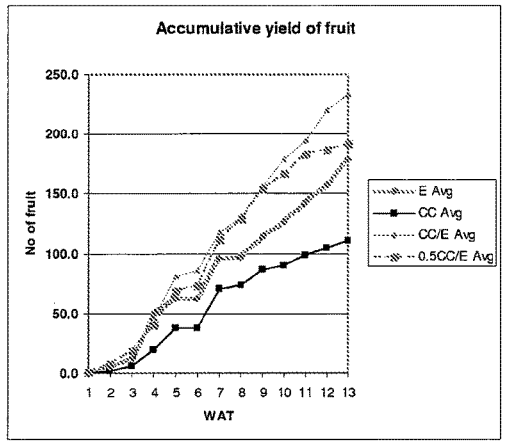
FIG. 26 is a graph that shows the effect of ComCat® (CC), Elementol R (E) and combinations thereof on changes in accumulative number of fruit harvested from 3 plants per group over a period of 13 weeks as described in Example 18.
Figure 27:
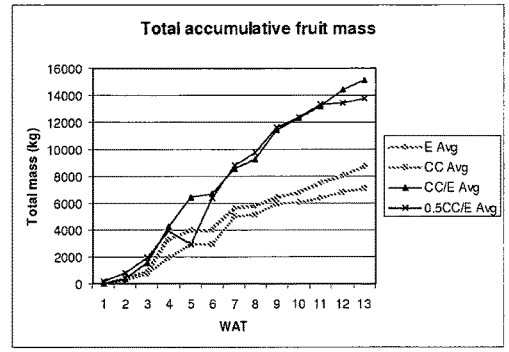
FIG. 27 is a graph that shows the total accumulative fruit mass observed from plants treated with ComCat® that is entrapped in Elementol R as compared to the increase observed with Elementol R or ComCat® individually as described in Example 18.

The % enhancement in terms of yield was calculated as 99% and 81% CC/E and 0.5CC/E respectively and total harvested mass as 199% and 204% for CC/E and 0.5CC/E respectively when compared with that obtained with CC. The enhancement of 33% and 21% for CC/E and 0.5CC/E respectively is far less when compared to Elementol, which on its own caused an increase in fruit yield and mass (FIGS. 26 and 27). Elementol as novel carrier molecule was demonstrated to be an efficient translocator of ComCat® molecules. It would also indicate that Elementol R enhanced the uptake of ComCat© to exert its bio-stimulatory effect. A synergistic effect of these two products may also come into play.

3.2 Moisture % and Fresh and Dry Mass (Fm:Dm) Ratios
3.2.1 Lettuce

All treatments had a stimulatory effect on the plant Fm:Dm ratios.

3.2.2 Tomatoes

Figure 28:
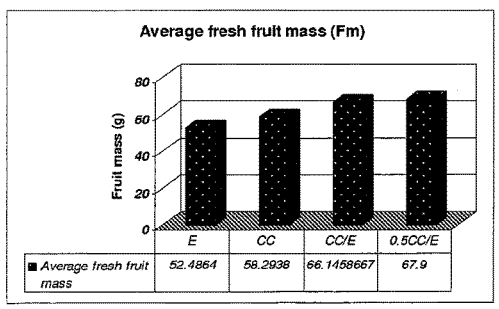
FIG. 28 is a graph that shows the increase in fresh fruit mass by the combination of Elementol R and CC as described in Example 18.

CC alone showed a higher average fresh fruit mass than E alone. However, pre-entrapment of CC into E increased the average fresh mass of the tomatoes still further (see FIG. 28). No significant difference was observed between CC/E and 0.5CC/E, except for week 13 and as the standard deviation on Fm is quite large, it may not be significant.

4. Physiological Related Parameters in Lettuce

4.1 Protein Content: Measured One Week after Each Treatment

Protein content was highest in week 2 and showed a decrease over the 12 weeks of the trial for all treatments. From weeks 4 to 12 CC had on average the least amount of proteins. In the final week all plants had relatively the same amount of proteins. The CC/E combination had the best stimulatory effect on proteins.

4.2 Respiration Rate

Figure 29:
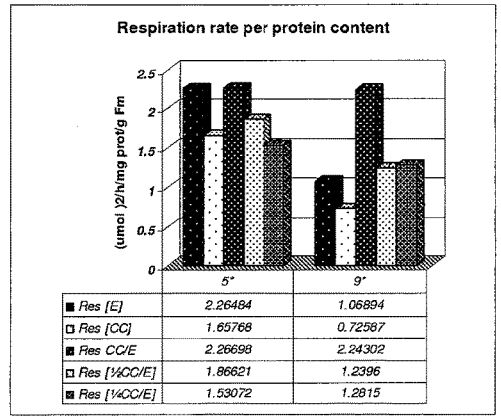
FIG. 29 is a graph that shows the respiration rate per protein content after the first administration (week 5) and the second administration (week 9) of the Elementol R, Comcat® and combination treatment as described in Example 18.

All plant treatments showed relatively the same respiration rate. In week 9 the CC/E treated plants had the best respiration rate. Respiration rate decreases until week 9 except for CC/E combination and increases again the last 4 weeks. All plant treatments show this "U" shape, due to higher energy requirements during early growth and flowering. The CC/E combination is the only treatment to show an increase in respiration rate (FIG. 29). Thus in week 9, the CC/E combination treatment had a stimulatory effect on the plants. All treatments involving E had a higher respiration rate during this week than CC alone.

When the respiration rate is expressed in terms of the amount of protein a fluctuation is observed. The respiration per amount of protein for the CC/E treated plants show an increase every time after the plants had been treated (week 5 and week 9; see FIG. 29). Thus the combination of E and CC stimulates respiration rate per mg of protein. At the end of week 13 the E plants had the highest respiration rate per mg protein, probably because the Elementol R treated plants flowered before plants treated with CC or combinations of CC and E, requiring a high respiration rate to supply adequate amounts of energy for flowering.

4.3 Photosynthesis Rate

Again during week 9 the photosynthesis rate for CC/E was very high. In week 11 the photosynthesis rate dropped considerably indicating that the stimulation caused by CC/E may be of short duration. At the end of week 13 the ¼CC/P combination group showed the highest photosynthesis indicating that the ¼CC/P combination stimulates photosynthesis for longer. Expressing photosynthesis rate in terms of the amount of protein present results in roughly the same result as respiration per mg protein, except that the ¼CC/P treated plants show the highest photosynthesis rate at the end of week 13, indicating that this treatment may have a longer lasting effect on photosynthesis rate per mg protein.

Photosynthesis must always exceed respiration rate. The higher the gain of photosynthesis on respiration, the higher the accumulation of carbons, resulting in the synthesis of more sugars. More sugars can be respired and thus the gain of energy is better. This energy acts as "fuel" for metabolic pathways. Bigger ratios result in better growth. Again the ¼CC/P combination shows an increase in photosynthesis:respiration ratio from week 5 to week 13. This combination has the best ratio at the end of week 13.

4.4 Chlorophyll Content

Figure 30:
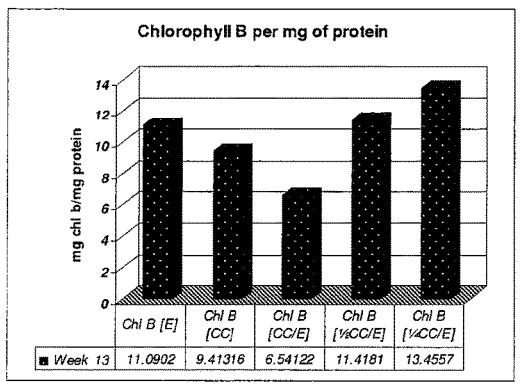
FIG. 30 is a graph that illustrates the comparative amounts of chlorophyll B per mg of protein as determined in week 13 of the trial described in Example 18.

Despite fluctuations an overall increase in chlorophyll a can be seen. By placing the amount of chlorophyll a in correlation with the amount of protein present in the plant shows the following. The E treatment has the most chlorophyll a per mg of protein for week 13, followed firstly by ¼CC/E, secondly by ½CC/E, and thirdly by CC/E, then by CC. Thus the least amount of CC in combination with E stimulates chlorophyll A the most (see FIG. 30 which is a graph that illustrates the comparative amounts of chlorophyll B per mg of protein as determined in week 13 of the trial.) CC had an inhibitory effect on the amount of chlorophyll B and this inhibitory effect is enhanced by the entrapment of CC in Elementol R vesicles. However, dilution of the CC concentration led to an increase in chlorophyll B/mg protein. Thus the dosage of the CC should be decreased when entrapped in Elementol R.

Figure 32:
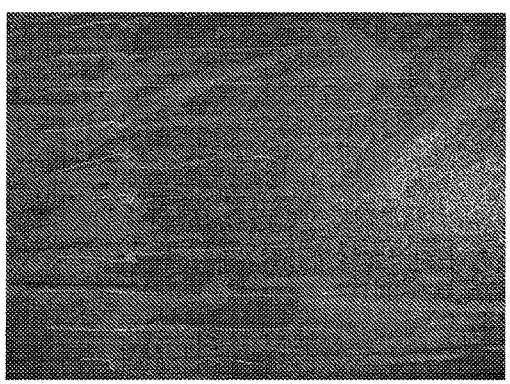
FIG. 32 is a photograph of germinating radishes on germination paper in the in vitro study described in Example 19.

Chlorophyll B showed a similar pattern. In the case of chlorophyll B, an overall increase is observed. In FIG. 32 the amount of chlorophyll B per mg of protein is shown. Here the ¼CC/E combination and ½CC/E combination also shows the best chlorophyll B concentration per mg of protein. E also has a high concentration of chlorophyll B per mg of protein. Thus lower amounts of CC used with E stimulated both chlorophyll A and B synthesis. CC inhibited chlorophyll B content, but the combination of CC/E inhibited the amount of chlorophyll B dramatically, illustrating that pre-entrapment in E enhanced the uptake and translocation of CC. The dilution of CC by 75% seemed to have negated the inhibitory effect of the CC. For this inhibitory effect to take effect, the entrapment of the CC in E had to have resulted in a dose-dependent uptake and translocation of the CC by E, as can be observed in FIG. 30.

4.5 Sugar Content

Both glucose and sucrose content is stimulated by the entrapment of CC in E. The sugar content of the plants are similar for CC and E, but the combination of CC/E increased the sucrose content by an average of 91% and that of glucose by an average of 64%. Again an increase of both sucrose and glucose concentration is found as the strength of the Com-Cat® decreases.

4.6 Brix

In the table below the Brix measurements with $HClO_4$ as background is presented. Brix values measures all dissolved substances present in the lettuce leaf and not only the sugar or sucrose content. Brix is in fact used to determine quality of lettuce. A high Brix reading indicates many dissolved substances as well as many sugars which indicate a good quality and healthy leaf. This may have contributed to low growth rates and poorly developed plants.

Figure 31:
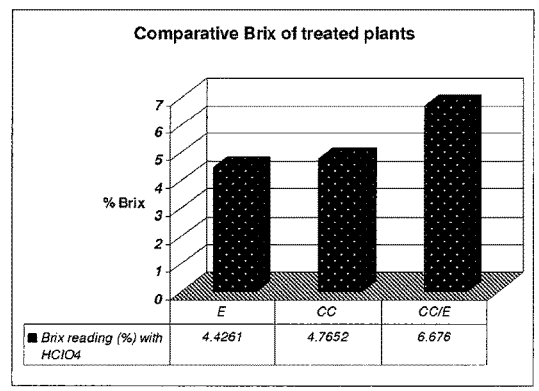
FIG. 31 is a graph that shows the comparative Brix readings in week 13 for Elementol R treated, CC treated and the combination treated plants described in Example 18 with $HClO_4$ as background.

Average Brix readings for treated plants with $HClO_4$ (see also FIG. 31)

| Treatment | Brix reading (%) |
| --- | --- |
| E | 4.4261 ± 0.2867 |
| CC | 4.7652 ± 0.3586 |
| CC/E | 6.6760 ± 0.5235 |

The enhancement in Brix readings by the combination is indicative of the higher uptake and translocation of CC by the Elementol carrier.

EXAMPLE 19

In Vitro and In Vivo Effect of Elementol R on Seedling Growth

1. Aims of the Study

To investigate the effect of Elementol R on germination and seedling growth in both C3 and C4 plants. In the process of photosynthesis, $CO_2$ and water are substrates and carbohydrates and oxygen are the products (Jakob and Heber 1996). Plants are classified as C3, C4 or CAM according to their mechanism of photosynthesis. The $C_3$ path involves the Calvin cycle, whereas the $C_4$ path uses a cycle where 3-phosphoglyceric acid is not the first product. $C_4$ photosynthesis provides a mechanism for high rates of carbon assimilation and is more resistant to the process of photo respiration.

The inherent effect of Elementol R on its own and mixed with an antifungal (see maize field trials below) were investigated.

2. In Vitro Effect of Elementol R on Seedling Growth

The conditions in terms of humidity and temperature were controlled as described in Examples 16 to 18. Three groups of radish seed were treated as follow:

| Group | Control | Elementol 125 | Elementol 250 |
|---|---|---|---|
| Dosage | 20 l Water/ha | 125 ml/20 l/ha | 250 ml/20 l/ha |
| Abbreviation | C | E125 | E250 |

Seeds were soaked in the above treatments overnight and then exposed to germination paper. The effect of the different treatments was measured with regards to its influence on radish root length (see FIG. 32 which is a photograph of germinating radishes on germination paper in the in vitro study described in Example 19. The increased root length on both sides of the short control seedlings is due to both faster germination and growth.). An enhancement in root length above control of 53.3 and 52.6% was observed for Ep125 and 250 respectively.

3. In Vivo Effect of Elementol R on Seedling Growth in Glass House Trials

The following study was done on wheat in glass house trials:

Cultivar: Wheat Kariega

The growing conditions in terms of temperature and relative humidity were relatively constant. Plants were planted in earth and irrigated by drip irrigation.

The treatments consisted of two groups: a reference group (RG) receiving fertilizer and a test (E) group receiving Elementol R. Seeds of the reference group were planted with fertilizer (3:1:0) according to supplier's instructions. Plants were treated with Elementol R at the three leave stage with similar concentrations than that described for the in vitro trial above, but with 20 ml E/100 L/ha at both the flag leave and just before flowering. Treatment was administered through foliar application. The trial outlay consisted of a randomized block design and ran for 3 and half months.

The following parameters were investigated weekly:
Any signs of phytotoxicity,
Differences in seedling size and height

| Wheat coleoptile's average growth (mm) | | | |
|---|---|---|---|
| Control | Ep 125 | Ep 250 | Ep 500 |
| 22 | 24 | 27 | 28 |

Figure 33:
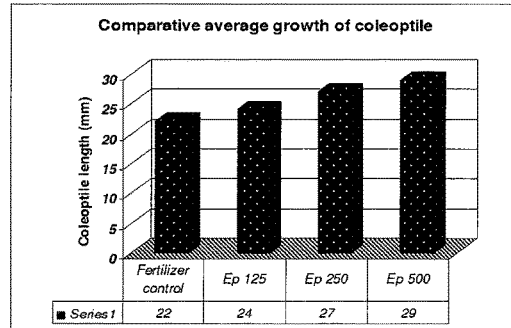
FIG. 33 is a graph that illustrates the comparative average length measured for coleoptiles of wheat for the fertilizer control, and the various dosages of Elementol R described in Example 19.

The table above illustrates the early response in small seedlings, but is representative of the general response. The growth response varied proportionately with the amount of dose of Elementol. The administration of Elementol R resulted in a linear dose response in terms of wheat coleoptile growth (see FIG. 33 which is a graph that illustrates the comparative average length measured for coleoptiles of wheat for the fertilizer control, and the various dosages of Elementol R.) The standard deviation from the linear dose response is exceptionally small, indicating a high confidence level in the data. Such a linear dose response can be used to indicate that a specific intervention on a biological system results in a specific response. Thus the response in coleoptile growth is specifically due to the administration of a specific dose of Elementol R. FIG. 33 shows that the maximum dose has not been reached and that further enhancement in growth may be possible with a higher dose. The enhancement in growth, using a dose of 500 ml/ha Elementol R was calculated to be 27.3%. No signs of toxicity (leaf burn, necrosis etc.) were observed.

4. Field Trials 4.1 In Vivo Effect of Elementol R in Wheat Field Trials

The cultivar was PAN 3377. Wheat was cultivated according to normal farming practices in the Central Free State, South Africa.

As in the glass house trials, the two groups consisted of a fertilizer control (3:2:1) and Elementol R at dosage of 500 ml/100 L water/ha). Treatment was limited to a single application at the three leave stage. The trial outlay was a randomized block design. The trial lasted 7 months.

Figure 34:
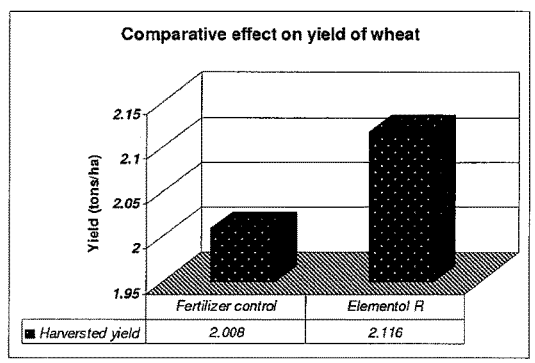
FIG. 34 is a graph that shows the enhancement in the yield of grain from wheat by a single administration of Elementol R cultivated in field trials as described in Example 19.

The yield was determined and is presented in FIG. 34. An average increase of 108 kg in yield per hectare was observed with the Elementol R treated group as compared to the reference fertilizer group. No phytotoxicity was observed.

4.2 In Vivo Effect of Elementol R in Pea Field Trials

Peas were cultivated according to normal farming practices on the farm Koedoesfontein in the Northern Free State, South Africa, with the following exception: 100 dry peas each were soaked overnight in either 500 ml borehole water (control group) of 5% Elementol R. The diluent was water from the same source. While peas from the control group absorbed all water during soaking, peas from the Elementol group absorbed only 300 ml of the 5% Elementol R. Peas were planted in two separate blocks to prevent any possible contamination between the two groups. The plants were irrigated by daily sprinkling.

Germination and seedling growth was observed from day 7. On day 10 a comparison was made of the number of seedlings that measured at least 300 mm in height in each block. In the block where the seeds were soaked in Elementol R, 57 seedlings were counted on day 10, whereas 18 seedlings were present in the control group. This represents an enhancement in germination and seedling growth of 3.1 times. Furthermore, the germination of the Elementol R group needed only 0.6 times as much water as the control group. This aspect may prove to very valuable in dry regions.

4.3 In Vivo Effect of Elementol R in Dry Maize Field Trials

A genetically modified cultivar, supplied by a large seed producing company was used. One bag of treated seed was split and one portion of the seeds in the bag was treated with Captan, while another portion was treated with Captan mixed with Elementol R in the following manner. Captan is a broad-spectrum contact fungicide that has been used on corn seed since the 1950s. It is usually dyed pink and leaves a pink dust in the seed bag and planter box. It is very effective against a broad range of soil fungi. The prescribed amount of Captan was mixed directly with the seeds (Captan reference group). For the test group, seeds were mixed with a similar amount of Captan in 2% Elementol R. The seeds of both groups were briefly mixed or stirred with their individual treatment and then left to dry. Seeds were planted in blocks of 3 or 5 rows stretching the length of the maize field with untreated block s on both sides of each of the treatment groups in the North West Province, South Africa. Culturing was done according to general farming practices with no irrigation.

Plants of each of the untreated, the reference Captan group and the Elementol R/Captan group were collected by pulling up every fifth plant in a row. Plant collection started 5 m into the field and continued towards the centre of the field until fifty plants of each group were collected.

Figure 35:
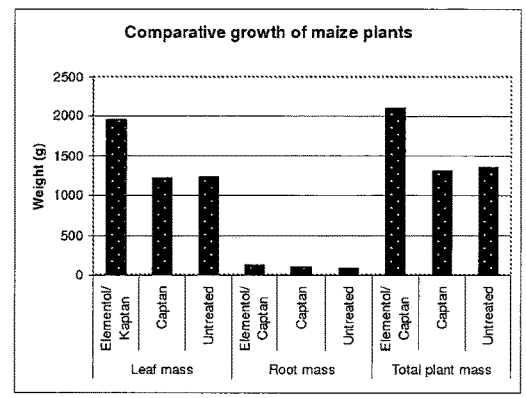
FIG. 35 is a graph that shows the average comparative plant, root and leaf weights of maize plants cultivated from seeds treated with the fungicide Captan, with a combination of Captan and Elementol R or with untreated seeds as described in Example 19.

The total plant mass, the root mass and the leaf mass of each plant were determined. FIG. 35 shows the comparative average masses for each of the group. Untreated seeds acted as control. Treatment of the seeds with Captan alone did not result in any change of growth of the plant leaves, and only slightly enhanced root mass, whereas seeds treated with the 2% Elementol R/Captan mix showed increases in leaf mass, root mass and therefore total plant mass.

Many variations of the invention may be devised without thereby departing from the spirit of the invention as formulated in the above statements of the invention.

EXAMPLE 20

Translocation of Elementol Vesicles Prepared with $CO_2$ in Stead of $N_2O$

Elementol C was prepared as described in Preparation 1 for Elementol B but $CO_2$ was used as gas during the preparation procedure. The size of the vesicles was determined to range between 300 nm and 2 µm. The z-potential was measured as −44 mV, using a Malvern Z-sizer.

The vesicles dispersed in the $CO_2$ containing Elementol C was labelled fluorescently with Nile red to a final concentration of 1 µM. Using a brush, a leaf of an ivy plant was painted with this mixture. A control of water was painted on the leaf of a second ivy plant. After 30 minutes, the leaves on the opposite side of the painted leaves were collected and investigated for the presence of fluorescence, using confocal laser scanning microscopy as described in Example 6, Study 1. Fluorescent vesicles were present in the collected leaf of the plant painted with the fluorescently labelled Elementol C, whereas no such fluorescence was found in the leaf collected from the plant painted with water. The fluorescence did not correspond to the auto fluorescence observed for chloroplasts or thylakoid membranes. The fluorescence observed in the test leaf was thus shown to be the result of translocation from one leaf to the opposite leaf by the $CO_2$ containing Elementol C.

Molecular modelling indicates that the relevant properties of nitrous oxide and carbon dioxide in the preparation of Elementol vesicles and microsponges are shared by carbon oxy sulphide.

The invention claimed is:

1. A liquid foliar spray composition comprising a microemulsion of long chain fatty acid based vesicles or microsponges with an aqueous carrier as a phytoloqically beneficial substance for a plant, wherein the long chain fatty acid based vesicles or microsponges is at least one substance selected from the group consisting of oleic acid, linoleic acid, alpha-linolenic acid, gamma-linolenic acid, arachidonic acid, eicosapentaenoic acid [C20:5ω3], decosahexaenoic acid [C22:6ω3], ricinoleic acid, Vitamin F Ethyl Ester, $C_1$ to $C_5$ alkyl esters thereof, glyceropolyethylene glycol esters thereof, and reaction products of hydrogenated and non-hydrogenated ricinoleic acid based oils with ethylene oxide, wherein a gas is dissolved in the long chain fatty acid based vesicles or microsponges, and wherein the long chain fatty acid based vesicles or microsponges have phytoloqically beneficial effects on the plant and wherein said composition is devoid of plant nutrients, plant pesticides, plant growth regulators, plant immune modulators, biostimulants, and genetic materials, and wherein the composition is a sprayable liquid.

2. The composition of claim 1, wherein at least 95% of the vesicles or microsponges are of a diametrical size of between 50 nm and 5 micrometer.

3. The composition of claim 1, wherein the micro-emulsion has a zeta potential of between −35 mV and −60 mV.

4. The composition of claim 1, wherein the long chain fatty acid based vesicles or microsponges of the micro-emulsion are made up of both of eicosapentaenoic acid [C20:5ω3] and decosahexaenoic acid [C22:6ω3].

5. The composition of claim 1, wherein the long chain fatty acid based vesicles or microsponges of the micro-emulsion are made up of a reaction product of ricinoleic acid based oils with ethylene oxide.

6. The composition of claim 5, wherein the reaction product of ricinoleic acid based oils with ethylene oxide is produced from castor oil.

7. The composition of claim 1, wherein the gas is selected from the group consisting of nitrous oxide, carbon oxysulfide and carbon dioxide.

8. A method of administering the liquid foliar spray composition of claim 1 to a plant, comprising the step of applying the composition to the plant by spraying the composition on the plant.

9. A plant growth stimulating micro-emulsion comprising fatty acid based vesicles or microsponges with an aqueous carrier, the fatty acid based vesicles or microsponges comprising at least one long chain fatty acid based substance selected from the group consisting of oleic acid, linoleic acid, alpha-linolenic acid, gamma-linolenic acid, arachidonic acid, eicosapentaenoic acid [C20:5ω3], decosahexaenoic acid [C22:6ω3], ricinoleic acid, $C_1$ to $C_5$ alkyl esters thereof, glyceropolyethylene glycol esters thereof, and reaction products of hydrogenated and non-hydrogenated ricinoleic acid based oils with ethylene oxide, wherein a gas is dissolved in the fatty acid based vesicles or microsponges, wherein said vesicles or microsponges entrap a complex of an amino acid in complex with, but not chelated to a plant nutrient that is a source of at least one element selected from the group consisting of carbon, hydrogen, oxygen, nitrogen, phosphorous, potassium, calcium, magnesium, sulphur, iron, manganese, zinc, copper, boron, molybdenum and chloride, wherein the plant growth stimulating micro-emulsion has phytoloqically beneficial effects on the plant and wherein said plant growth stimulating micro-emulsion is devoid of plant pesticides, plant growth regulators, plant immune modulators, biostimulants, and genetic materials, and wherein the microemulsion is a sprayable liquid.

10. A method of administering the plant growth stimulating micro-emulsion of claim 9 to a plant, comprising the step of spraying the micro-emulsion on the plant.

11. The composition of claim 1, wherein said aqueous carrier is water.

12. The composition of claim 9, further comprising dl-alpha-tocopherol.

13. The composition of claim 9, further comprising unsaturated fatty acids in addition to and different from said at least one long chain fatty acid based substance.

* * * * *

UNITED STATES PATENT AND TRADEMARK OFFICE
CERTIFICATE OF CORRECTION

PATENT NO. : 10,321,681 B2  
APPLICATION NO. : 14/206251  
DATED : June 18, 2019  
INVENTOR(S) : Anne Frederica Grobler Page 1 of 1

It is certified that error appears in the above-identified patent and that said Letters Patent is hereby corrected as shown below:

In the Claims

Column 49, Claim 1, Line 60: replace "phytoloqically" with --phytologically--

Column 50, Claim 1, Line 7: replace "phytoloqically" with --phytologically--

Column 50, Claim 9, Line 56: replace "phytoloqically" with --phytologically--

Signed and Sealed this  
Sixth Day of August, 2019

Andrei Iancu  
*Director of the United States Patent and Trademark Office*